(12) United States Patent
Lepilleur et al.

(10) Patent No.: US 8,003,585 B2
(45) Date of Patent: *Aug. 23, 2011

(54) CATIONIC POLYMERS AND FIXATIVE APPLICATIONS THEREFOR

(75) Inventors: Carole A. Lepilleur, Akron, OH (US); Denise W. Rafferty, Sagamore Hills, OH (US); Joseph A. Zellia, Barberton, OH (US); Jeffrey A. Fruscella, Mentor, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/839,435

(22) Filed: Jul. 20, 2010

(65) Prior Publication Data

US 2010/0284955 A1 Nov. 11, 2010

Related U.S. Application Data

(63) Continuation of application No. 12/211,494, filed on Sep. 16, 2008, now Pat. No. 7,759,296, and a continuation-in-part of application No. 11/843,920, filed on Aug. 23, 2007, now Pat. No. 7,439,214, and a continuation of application No. 10/874,296, filed on Jun. 18, 2004, now Pat. No. 7,262,157.

(60) Provisional application No. 60/479,793, filed on Jun. 19, 2003.

(51) Int. Cl.
*C11D 3/22* (2006.01)
*C11D 3/37* (2006.01)
*C11D 1/38* (2006.01)
*A61K 8/73* (2006.01)

(52) U.S. Cl. ........ 510/121; 510/151; 510/470; 424/488; 424/70.13; 424/78.03

(58) Field of Classification Search .................. 510/121, 510/151, 470; 424/488, 70.13, 78.03
See application file for complete search history.

(56) References Cited

U.S. PATENT DOCUMENTS

| | | | |
|---|---|---|---|
| 2,798,053 | A | 7/1957 | Brown |
| 3,657,175 | A | 4/1972 | Zimmerman |
| 4,031,307 | A | 6/1977 | DeMartino et al. |
| 4,131,576 | A | 12/1978 | Iovine et al. |
| 4,384,096 | A | 5/1983 | Sonnabend |
| 4,464,524 | A | 8/1984 | Karickhoff |
| 4,509,949 | A | 4/1985 | Huang et al. |

(Continued)

FOREIGN PATENT DOCUMENTS

EP 0486135 B1 4/1995

(Continued)

OTHER PUBLICATIONS

M.J. Reiger, Ph.D. (ed.), Evaluation of Performance, Ch. 30, Harry's Cosmeticology, 8th Ed., pp. 666-667, Chemical Publishing Co., Inc. New York, NY, 2000.

(Continued)

*Primary Examiner* — Brian P Mruk
(74) *Attorney, Agent, or Firm* — Thoburn T. Dunlap

(57) ABSTRACT

This invention relates to cationic *Cassia* polymers and to their use in hair fixative applications. The cationic *Cassia* polymers demonstrate superior stiffness profiles and a high level of curl retention when subjected to high humidity conditions for extended periods of time.

16 Claims, 3 Drawing Sheets

U.S. PATENT DOCUMENTS

| | | | |
|---|---|---|---|
| 4,645,833 A | | 2/1987 | Bayerlein et al. |
| 4,753,659 A | * | 6/1988 | Bayerlein et al. ................. 8/561 |
| 4,801,671 A | | 1/1989 | Shay et al. |
| 5,087,445 A | | 2/1992 | Haffey et al. |
| 5,136,063 A | | 8/1992 | O'Lenick, Jr. |
| 5,180,843 A | | 1/1993 | O'Lenick, Jr. |
| 5,292,843 A | | 3/1994 | Jenkins et al. |
| 5,294,299 A | | 3/1994 | Zeuner et al. |
| 5,733,854 A | | 3/1998 | Chowdhary et al. |
| 7,205,271 B2 | | 4/2007 | Drzewinski et al. |
| 7,262,157 B2 | * | 8/2007 | Utz et al. ...................... 510/121 |
| 7,378,479 B2 | | 5/2008 | Tamareselvy et al. |
| 7,439,214 B2 | * | 10/2008 | Utz et al. ...................... 510/121 |
| 7,704,934 B2 | * | 4/2010 | Lepilleur ...................... 510/121 |
| 7,759,296 B2 | * | 7/2010 | Lepilleur et al. ............. 510/121 |
| 2005/0075497 A1 | | 4/2005 | Utz et al. |
| 2005/0129643 A1 | | 6/2005 | Lepilleur et al. |
| 2006/0099167 A1 | * | 5/2006 | Staudigel et al. .......... 424/70.13 |
| 2007/0292380 A1 | | 12/2007 | Staudigel et al. |
| 2008/0206355 A1 | | 8/2008 | Schwartz et al. |
| 2009/0010855 A1 | | 1/2009 | Lepilleur et al. |
| 2009/0137438 A1 | | 5/2009 | Lepilleur et al. |

FOREIGN PATENT DOCUMENTS

| | | |
|---|---|---|
| WO | 93/11103 A1 | 6/1993 |
| WO | 2004/112733 A1 | 12/2004 |
| WO | 2006/062792 A2 | 6/2006 |
| WO | 2006/065469 A1 | 6/2006 |
| WO | 2007/136708 A2 | 11/2007 |
| WO | 2008/063471 A2 | 5/2008 |
| WO | 2008/079317 A2 | 7/2008 |
| WO | 2009/011677 A1 | 1/2009 |
| WO | 2009/107062 A2 | 9/2009 |

OTHER PUBLICATIONS

Gregory D. Shay, Chapter 25, Alkali-Swellable and Alkali-Soluble Thickener Technology—A Review, Polymers in Aqueous Media, Advances in Chemistry Series 223, J. Edward Glass (ed.), ACS, pp. 457-494, Division Polymeric Materials, Washington, DC, 1989.

Penelope Diaz et al., Set Relaxation of Human Hair, J. Soc. Cosmet. Chem., 34, pp. 205-212, Jul. 1983.

Charles Todd et al., Volatile Silicone Fluids for Cosmetic Formulations, Cosmetics and Toiletries, vol. 91(1), pp. 29-32, 1976.

Kenneth A. Kasprzak, Volatile Silicones, Soap/Cosmetics/Chemical Specialties, pp. 40-43, Dec. 1986.

J.A. Staudigel et al., Use of Quaternized Cassia Galactomannan for Hair Conditioning, Journal of Cosmetic Science, Society of Cosmetic Chemists, New York, NY, US, vol. 58, No. 6, Jan. 1, 2007, pp. 637-650.

* cited by examiner

CATIONIC POLYMERS AND FIXATIVE APPLICATIONS THEREFOR

CROSS REFERENCE TO RELATED APPLICATION

This application is a continuation of U.S. application Ser. No. 12/211,494 filed on Sep. 16, 2008, now U.S. Pat. No. 7,759,296, which is a continuation-in-part of Ser. No. 11/843, 920 filed on Aug. 23, 2007, now U.S. Pat. No. 7,439,214, which is a continuation of U.S. application Ser. No. 10/874, 296, filed on Jun. 18, 2004, now U.S. Pat. No. 7,262,157, which claims priority from U.S. Provisional Application Ser. No. 60/479,793, filed on Jun. 19, 2003.

TECHNICAL FIELD

This invention generally relates to polygalactomannan derivatives. More specifically, the invention relates to cationically functionalized galactomannan polymers obtained from *Cassia tora* and *Cassia obtusifolia* and their use in personal care, health care, household, institutional and industrial products and the like. The cationically functionalized galactomannan polymers can be employed as thickeners, stabilizers, emulsifiers, spreading aids, hair fixatives, and carriers for enhancing the efficacy, deposition and delivery of chemically and physiologically active ingredients. In addition, these polymers are useful for improving the psychosensory and aesthetic properties of cosmetic formulations in which they are included.

BACKGROUND

Polygalactomannans are polysaccharides that are found in the endosperm material of seeds from leguminous plants such as *Cyamopsis tetragonoloba* (guar gum), *Cesalpinia spinosa* (tara gum), *Ceratonia siliqua* (locust bean gum), and other members of the Leguminosae family. A polygalactomannan is composed of backbone of 1→4-linked β-D-mannopyranosyl units with recurring 1→6-linked α-D-galactosyl side groups branching from the number 6 carbon of a mannopyranose residue in the backbone. The galactomannan polymers of the different Leguminosae species defer from one another in the frequency of the occurrence of the galactosyl side units branching from the polymannopyranose backbone. The average ratio of D-mannosyl to D-galactosyl units in the polygalactomannan contained in guar gum is approximately 2:1, approximately 3:1 for tara gum, and approximately 4:1 for locust bean gum. Another important source of polygalactomannan is *Cassia tora* and *Cassia obtusifolia* (collectively known as *Cassia* gum). The average ratio of D-mannosyl to D-galactosyl units in the polygalactomannan contained in *Cassia* gum is at least 5:1.

Polygalactomannan obtained from *Cassia* gum is schematically represented in the structure below:

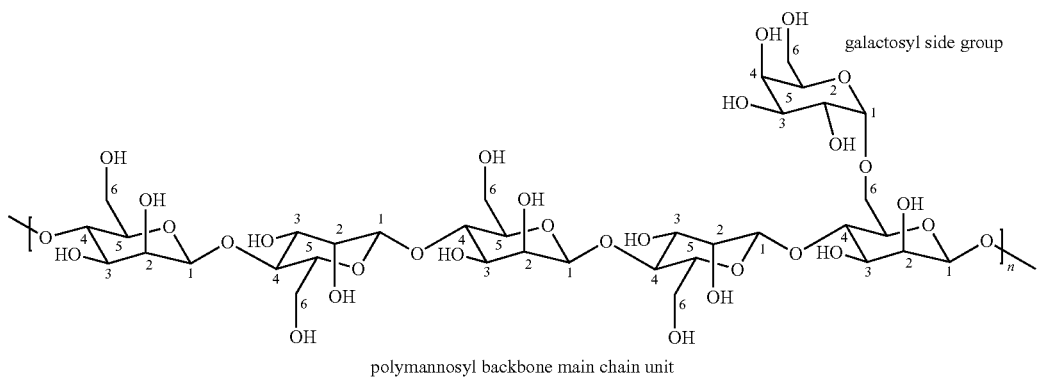

polymannosyl backbone main chain unit wherein n is an integer representing the number of repeating units in the polymer. The cationic polygalactomannan used in the practice of this invention typically has a weight average molecular weight (Mw) ranging from 200,000 to 3,000,000 Daltons in one aspect, 300,000 to 2,000,000 Daltons in another aspect, and 400,000 to 1,000,000 Daltons in a further aspect of the invention.

Polygalactomannans are hydrocolloids that have a high affinity for water. They have been widely used as suspending, thickening, emulsifying, and gelling agents in applications as diverse as foodstuffs, coatings, personal care compositions and in oil well fracturing fluids. Although the use of these polymers has been met with great success, polygalactomannans used in their natural form have suffered some drawbacks from a water solubility standpoint. An unsubstituted polymannose backbone is completely insoluble in water. The attachment of galactose side units to the C-6 atom in the recurring mannose residues of the polymannose backbone increases the water solubility of the polymer, particularly in cold water (i.e., ambient temperature and below). The greater the galactose side unit substitution, the greater is the cold water solubility properties of the polygalactomannan. Consequently, lower ratios of D-mannosyl to D-galactosyl units in the polygalactomannan leads to better cold water solubility. For example, guar gum polygalactomannan (average D-mannosyl to D-galactosyl ratio 2:1) is soluble in cold water; while *Cassia* gum polygalactomannan (average D-mannosyl to D-galactosyl ratio of 5:1) is only sparingly soluble in cold and hot water.

U.S. Pat. No. 4,753,659 to Bayerlein et al. discloses inter alia that improved cold water solubility can be imparted to *Cassia* gum by chemically modifying the polygalactomannan. Disclosed uses for the chemically modified *Cassia* gum polygalactomannans include textile printing applications, oil well drilling mud auxiliaries, and mining and explosive applications.

U.S. Pat. No. 5,733,854 to Chowdhary et al. discloses a chemically modified guar gum and a method for its preparation. According to Chowdhary et al., cationically functionalized guar gum polygalactomannans produce clear and colorless solutions upon dispersal in aqueous or organic solvents. A disclosed application for the cationically functionalized guar gum includes its incorporation into detergent compositions for human and household uses. Other disclosed uses include personal care and cosmetic applications. The use of cationically functionalized *Cassia* gum in hair fixative formulations is not discussed.

Accordingly, there exists is a need for a cationic polygalactomannan with a high degree of cationic functionalization which is suitable for use in thickener, stabilizer, emulsifier, spreading aid, hair fixative and in carrier applications for enhancing the efficacy, deposition and delivery of chemically, cosmetically and physiologically active ingredients.

The desire to have one's hair retain a particular set or coiffure is widely held. A common methodology for accomplishing this is by applying a "fixative" to the hair. Hair fixative compositions can assist in manipulating (styling) the hair, and provide temporary benefits in holding the shape of the hair style (fixing) and maintaining the shine or appearance (grooming, restyling) of the coiffure during the day or between hair washing periods with water or shampoo, or between subsequent hair setting procedures.

The term "fixative" as applied to the cationic *Cassia* polymers of the present invention encompasses the properties of film-formation, adhesion, or coating deposited on a keratinous surface (e.g., hair and skin) on which the polymer is applied. The terms "hair styling and hair fixative" as commonly understood in the hair care art, and as used herein, refer collectively to hair setting agents that are hair fixatives and film formers and which are topically applied to the hair to actively contribute to the ease of styling and/or holding of a hair set, and to maintain the restylability of the hair set. Hence, hair setting compositions include hair styling, hair fixative, and hair grooming products that conventionally are applied to the hair (wet or dry) in the form of gels, rinses, emulsions (oil-in-water, water-in-oil or multiphase), such as lotions and creams, pomades, sprays (pressurized or non-pressurized), spritzes, foams, such as mousses, shampoos, solids, such as sticks, semisolids and the like, or are applied from a hair setting aid having the hair setting composition impregnated therein or coated thereon, to leave the hair setting agent in contact on the hair for some period until removed, as by washing.

Various objective and subjective methods are used to measure the efficacy of a hair fixative composition. One method commonly employed evaluates the resistance of the hair set to high humidity conditions as a function of curl retention. When curl retention is measured under controlled ambient temperatures in the range of about 23° to about 27° C. and high humidity in the range of about 80 to 90% relative humidity (RH), it is commonly referred to as high humidity curl retention (HHCR). Most conventional hair fixative formulations are marginally effective, typically providing an HHCR of about 70% of the initial curl for a period of not more than about 0.75 hours. Thus there is an ongoing need for an increase in the HHCR of hair fixative or hair setting formulations.

One of the most common needs in the hair fixative market today is stiff hair feel and stiff hold. This is especially desirable in men's styling, in products targeting younger consumers, and in regions where hair is more tenacious and requires greater holding power such as Asia and Latin America. Thus, the demand for stiff hold is a growing trend. Traditional stiff-hold styling polymers have many deficiencies including poor humidity resistance, tackiness or stickiness and excessive flaking. Accordingly, there is an ongoing need for an easy-to-use polymer that provides both superior stiffness and superior high humidity style retention performance.

Also of importance are the aesthetic characteristics and appearance of hair fixative or hair setting compositions before, during, and after application to hair. In one aspect of the invention, the product viscosity should be non-runny to avoid dripping during application. In another aspect, product clarity is substantially transparent or clear in order to obtain a "clean" product appearance. The product should be easy to spread, have a smooth texture, a non-tacky feel, and be able to dry relatively quickly on the hair.

DESCRIPTION OF EXEMPLARY EMBODIMENTS

Figure 1:
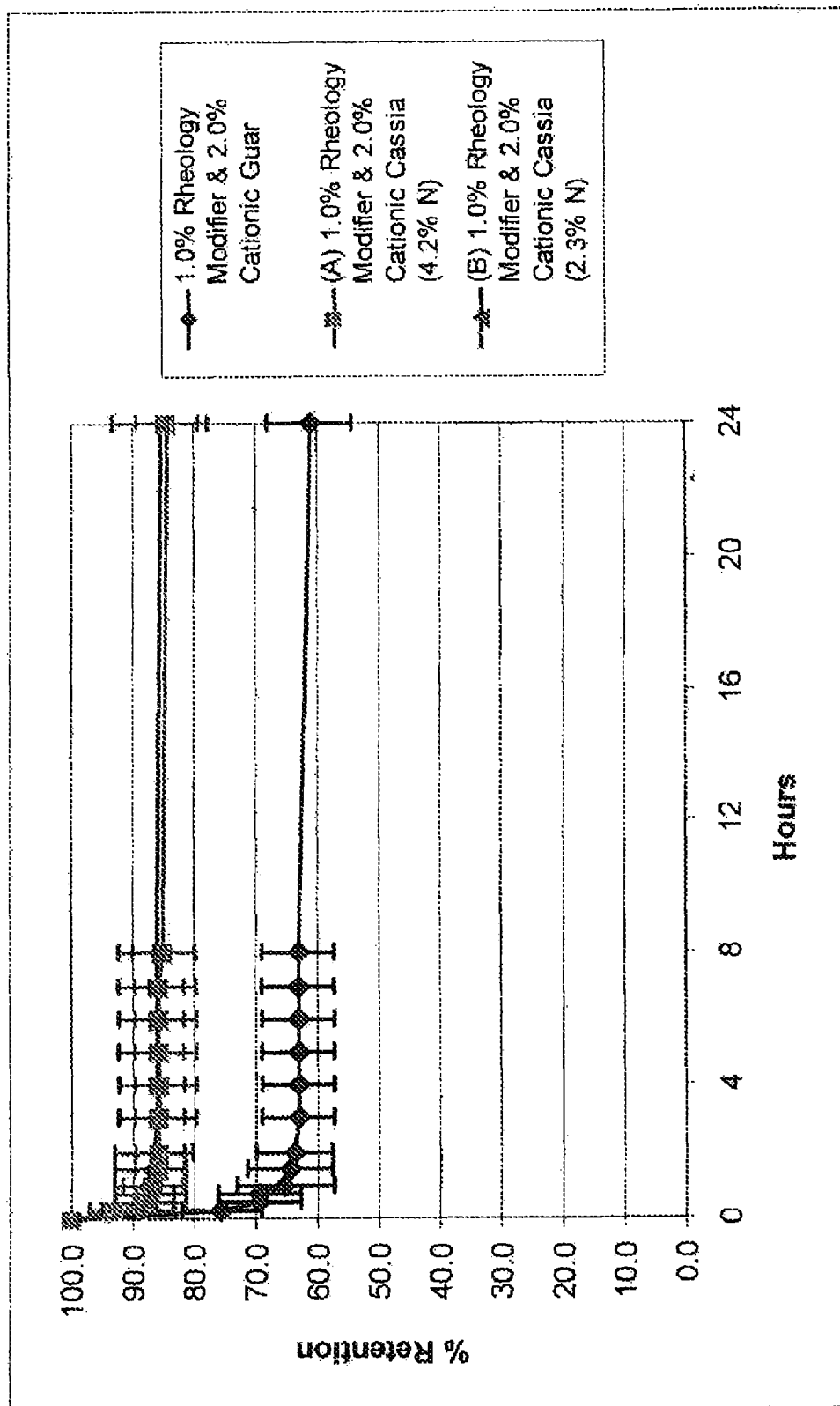
FIG. 1 is a plot comparing the percent of spiral curl retention under high humidity conditions of hair tresses treated with fixative compositions containing cationic *Cassia* of the present invention compared to hair tresses treated with an identically formulated fixative composition containing commercially available cationic guar.

Exemplary embodiments in accordance with the present invention will be described. Various modifications, adaptations or variations of such exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

One aspect of the present invention relates to the use of a cationically functionalized *Cassia* galactomannan polymer (*Cassia* polygalactomannan) as a fixative polymer having superior curl retention and stiffness properties. In one hair setting aspect, the efficacy of the hair fixative is evaluated herein by its ability to provide high humidity curl resistance or retention (HHCR) to the hair. HHCR refers to the resistance of a hair set to relaxation (i.e., reversion to its original configuration) or loss of curl when exposed to a high humidity in the range of about 90% relative humidity, measured in terms of % curl retention (CR) over selected time intervals as described in more detail herein.

In another hair setting aspect, the efficacy of the hair fixative is evaluated herein by its ability to provide high mechanical stiffness properties. Mechanical stiffness refers to the Peak Force, in Newtons, required to bend a fixative treated hair tress mounted on a three-point bending rig as described in more detail herein.

The cationic *Cassia* polymers of this invention can be employed as the sole fixative component in a hair fixative composition or can be formulated in combination with one or more hydrocolloid polymers, one or more rheology modifiers, one or more auxiliary fixative polymers, one or more adjuvants and additives; commonly employed in hair fixative compositions; and combinations thereof. Such hydrocolloid polymers, rheology modifiers, auxiliary fixative polymers, adjuvants and additives are described hereinbelow.

The cationic *Cassia* polymers of this invention can be formulated to obtain fixative products in the form of gels, rinses, emulsions (oil-in-water, water-in-oil or multiphase), such as lotions and creams, pomades, waxes, sprays, (pressurized or non-pressurized), spritzes, foams, such as mousses, shampoos, solids, such as sticks, semisolids and the like.

In one aspect of the invention, hair fixative formulations containing the cationic *Cassia* polymers can be delivered from water, water/organic solvent mixtures, or solvent/propellant systems. In another aspect, the cationic *Cassia* polymers are dissolved in a polar solvent, such as water or water-alcohol mixture.

The hair fixative compositions of the invention can be provided and dispensed from assorted package forms known in the art, i.e., pressurized and non-pressurized containers, such as cans, bottles, packets, ampoules, jars, tubes, and the like. In another packaged form embodiment, the hair fixative composition can be dispensed to the hair from a hair setting aid impregnated with the hair fixative composition or coated with the hair setting composition. The term "hair setting aid", as used herein, refers to wipes, pads, towlettes, sponges, curling papers, hair combs, hair brushes, hair curlers, such as sponge hair rollers, and the like, that can serve as substrates for holding and delivering cationic *Cassia* polymer to hair. The hair setting aid can be impregnated with hair fixative composition, such as by soaking, immersing, saturating, and the like, or the hair setting aid can be coated with the hair fixative composition, such as by brushing, spraying, dipping, and the like, and then packaged, while wet or in substantially dried form.

Hair fixative spray compositions can be dispensed from finger-actuated pump devices, either as pressurized aerosol sprays, mousses, spritzes, and foams containing propellant, or as non-pressurized, mechanically propelled sprays and foams. When a cationic *Cassia* polymer of the invention is formulated into a pressurized aerosol composition, the propellant can be any conventional hydrocarbon such as, for example, fluorinated hydrocarbons, selected from difluoroethane, tetrafluoroethane, hexafluoroethane, and mixtures thereof; dimethyl ether; liquid volatile hydrocarbons, such as, for example, propane, isobutene, n-butane and mixtures thereof; and compressed gas, such as, for example, carbon dioxide, nitrous oxide and nitrogen. The amount of propellant is governed by the spray characteristic and pressure factors desired as is well known in the aerosol art. In one aspect, pressurized aerosol hair fixative compositions contain concentrations of environmentally and physiologically acceptable solvent/propellant combinations that meet legislated federal and state governmental requirements for volatile organic compounds (VOC). For low VOC compositions, the solvent system in one aspect is water based. In another aspect, the solvent system can include at least about 20 wt. % to about 50 wt. % water. In another aspect, the solvent system contains not more than about 25 wt. % of organic solvent. For mousse products, the level of propellant can be in the range of about 1 wt. % to about 30 wt. % in one aspect, and from about 3 wt. % to about 15 wt. % in another aspect, based on the total weight of the fixative composition.

Foam hair fixative compositions can be of a "post-foaming" gel to a mousse type product where volatile liquid hydrocarbon is dispersed in the hair fixative composition and then packaged in a container, such as, for example, a bag-in-can, SEPRO-can, sealed and pressurized on the outside of the bag, as known in the art. Alternatively, foam hair fixative compositions can be a gel or mousse formulation that is mechanically aerosolized by placing it in a finger-actuated non-pressurized pump dispenser.

The hair fixative compositions of the invention can be formulated as hair cosmetic type products containing hair colorants, such as colorant styling gels or styling sticks for concurrently providing temporary hair color.

In one aspect, the present invention relates to *Cassia* polygalactomannans that are cationically functionalized to attain varying degrees of cationic group content which can be expressed as cationic charge density (hereafter referred to a charge density). In other aspects the present invention relates to cationically functionalized *Cassia* gum polygalactomannan that is tailored for use as a thickener, stabilizer, emulsifier, spreading aid, fixative, and carriers for enhancing the efficacy, deposition and delivery of chemically and physiologically active ingredients.

As used here and throughout the specification, the term "cationically functionalized" refers to a polymer that has been modified to contain a cationic group containing moiety. In the present invention, a cationic group containing moiety is reacted with a hydroxyl group(s) on the mannosyl and/or galactosyl units that comprise the *Cassia* polygalactomannan polymer. In the reaction the hydroxyl hydrogen is replaced by a moiety derived from the cationic functionalization reagent. In one embodiment, the hydroxyl hydrogen on the C-6 carbon atom is replaced by a moiety derived from the cationic functionalization reagent. The reaction is schematically represented below:

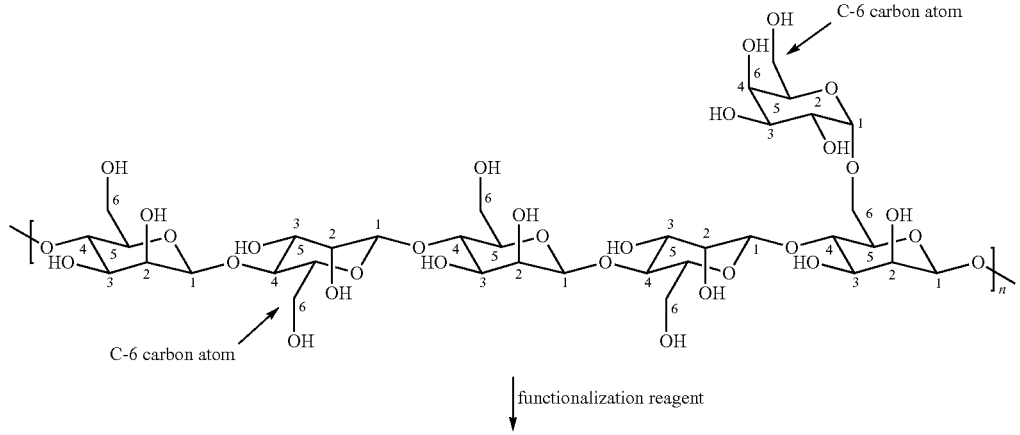

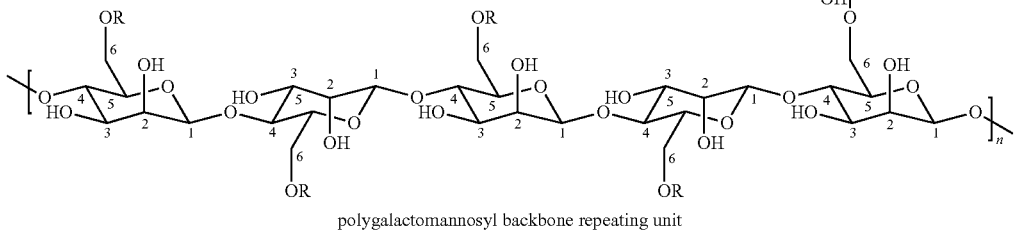

polygalactomannosyl backbone repeating unit

In some embodiments of the invention, R independently represents hydrogen or a cationic group, subject to the proviso that all R groups can not be hydrogen at the same time. In other embodiments, R independently is selected from the formula:

-AR$^1$ wherein A is an alkylene spacer group containing 1 to 6 carbon atoms and R$^1$ represents a cationic substituent. In another embodiment the alkylene group contains 2, 3, 4, or 5 carbon atoms. The alkylene spacer is optionally mono-substituted or multi-substituted with a group selected from C$_1$ to C$_3$ alkyl, C$_1$ to C$_3$ haloalkyl, C$_1$ to C$_3$ hydroxyalkyl, hydroxyl, halogen (bromine, chlorine, fluorine, and iodine), and combinations thereof; and n represents the number of repeating units necessary to attain a weight average molecular weight (Mw) ranging from 200,000 to 3,000,000 Daltons in one aspect, 300,000 to 2,000,000 Daltons in another aspect, and 400,000 to 1,000,000 Daltons in a further aspect of the invention.

Exemplary cationic substituents under R$^1$ includes cationic ammonium, sulfonium and phosphonium moieties represented by the radicals: —N(R$^3$)$_3$$^+$X$^-$, —S(R$^3$)$_2$$^+$X$^-$, —P(R$^3$)$_3$$^+$X$^-$, wherein R$^3$ independently represents C$_1$ to C$_{24}$ alkyl, benzyl and phenyl; and X is any suitable anion that balances the charge on the onium cation. In one embodiment, X is a halide anion selected from bromine, chlorine, fluorine and iodine. The alkyl, benzyl and phenyl substituents defined under R$^3$ can optionally be mono-substituted or multi-substituted with a group selected from C$_1$ to C$_3$ alkyl, hydroxyl, halogen (bromine, chlorine, fluorine, and iodine), and combinations thereof. Illustrative cationic groups defined under -AR$^1$ can be represented by the formulae:

-alkylene-N(R$^3$)$_3$$^+$X$^-$

-alkylene-S(R$^3$)$_2$$^+$X$^-$

-alkylene-P(R$^3$)$_3$$^+$X$^-$ wherein alkylene, R2, R3, and X are as previously defined. Representative of cationic groups under -AR$^1$ are quaternary ammonium groups that include but are not limited to the formula:

$$\text{—CHCHCH}_2\text{—}\overset{\overset{\displaystyle CH_3}{|}}{\underset{\underset{\displaystyle CH_3}{|}}{N^+}}\text{—}R^3 \quad Cl^-$$
$$\phantom{\text{—CH}}\underset{R^4}{|}\phantom{H}\underset{OH}{|}$$

wherein R$^3$ is selected from C$_1$ to C$_{24}$ alkyl, benzyl and phenyl in one aspect and methyl, decyl, dodecyl, butadecyl, cocoalkyl, dodecyl, and octadecyl in another aspect, and R$^4$ is selected from hydrogen and chlorine. In another aspect the quaternary ammonium group is 2-hydroxy-3-(trimethylammonium)propyl chloride represented by the formula:

$$\text{—CH}_2\text{CHCH}_2\text{—}\overset{\overset{\displaystyle CH_3}{|}}{\underset{\underset{\displaystyle CH_3}{|}}{N^+}}\text{—}CH_3 \quad Cl^-$$
$$\phantom{\text{—CH}_2}\underset{OH}{|}$$

Underivatized *Cassia* gum or flour is commercially available from Lubrizol Advanced Materials, Inc., Noveon® Consumer Specialties Division, under the Novegum™ trademark. In one aspect of the present invention the charge density of the cationically functionalized *Cassia* ranges from about 0.1 meq/g to about 7 meq/g, from about 0.5 meq/g to about 4 meq/g in another aspect, and from about 0.6 meq/g to about 3 meq/g in still another aspect. The charge density of a cationic polymer of the invention can be calculated as follows:

$$CD \text{ (meq/g)} = \frac{\text{Wt. \% of (Nitrogen, Sulfur, or Phosphorous) in the polymer}}{\text{Molecular Wt. of (Nitrogen, Sulfur, or Phosphorous)} \times 100} \times 1000$$

The functionalization of the *Cassia* polygalactomannan hydroxyl group(s) can be accomplished by methods well known to those skilled in the art. Generally speaking, a hydroxyl group on the *Cassia* polymer backbone can be reacted with any functionalization reagent containing a cationic moiety that is reactive therewith. For example, to cationically functionalize *Cassia* gum, a hydroxyl group(s) on the *Cassia* gum polygalactomannan is reacted with a functionalization reagent that contains a cationic substituent and a functional moiety that is reactive with a hydroxyl group. The functionalization reaction is conducted in an appropriate solvent and at an appropriate temperature. The amount of functional group substitution (i.e., charge density) can be controlled by adjusting the stoichiometric amount of the functionalization reagent added to the *Cassia* polygalactomannan. Functionalization methods for *Cassia* gum polygalactomannans are disclosed in U.S. Pat. No. 4,753,659 which is incorporated herein by reference. Additional methods of functionalizing polygalactomannans are set forth in U.S. Pat. No. 5,733,854.

While not intending to be bound by theory, it is surmised that the C-6 hydroxyl groups on the polygalactomannan are more reactive to functionalization than the C-2 and C-3 hydroxyl groups on the mannosyl and galactosyl units and the C-4 hydroxyl group on the galactosyl units due to steric considerations. Notwithstanding the foregoing, it is contemplated that any free hydroxyl group(s) on the polygalactomannan backbone can be functionalized with the cationic functionalization reagent. In this embodiment the cationically functionalized repeating unit can be represented as follows:

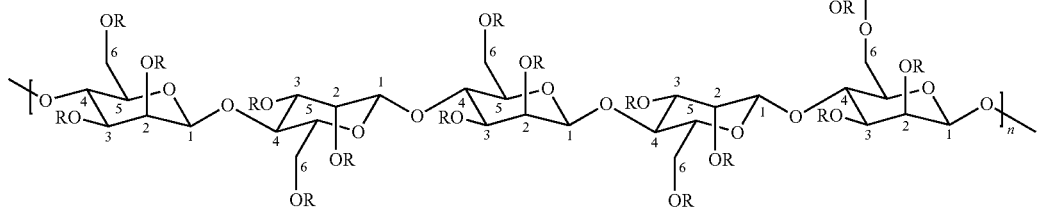

wherein R represents hydrogen or a cationic group, subject to the proviso that all R groups can not be hydrogen at the same time, and R and n are as previously defined.

In an exemplary reaction, *Cassia* gum polygalactomannan can be cationically functionalized with co-reactive quaternary ammonium compounds that contain a reactive epoxy group or a halohydrin group. In one such embodiment *Cassia* gum can reacted with glycidyltrimethylammonium chloride (75% aqueous solution) in an alkaline aqueous medium at a temperature of about 52° C. to yield the desired 2-hydroxy-3-(trimethylammonium)propyl *Cassia* galactomannan chloride product. The reaction is schematically represented below:

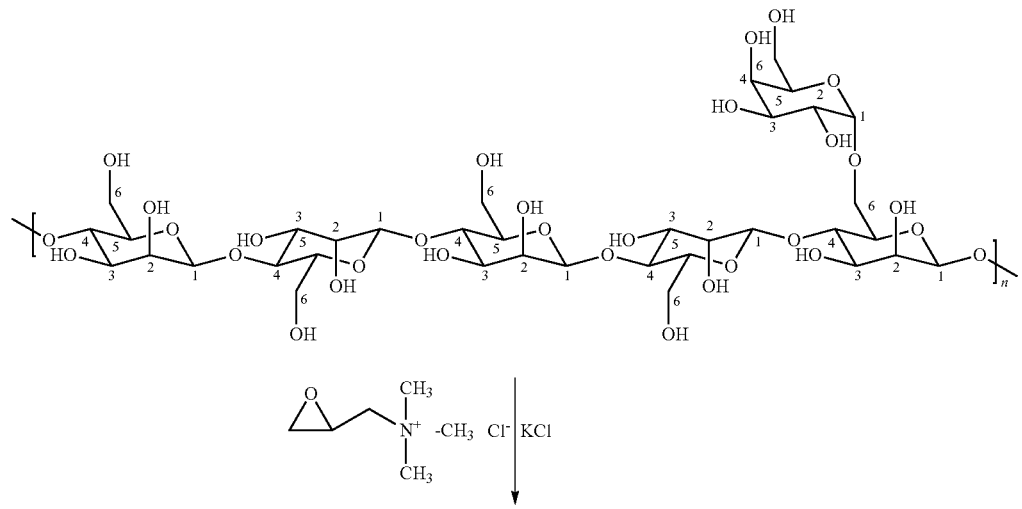

-continued

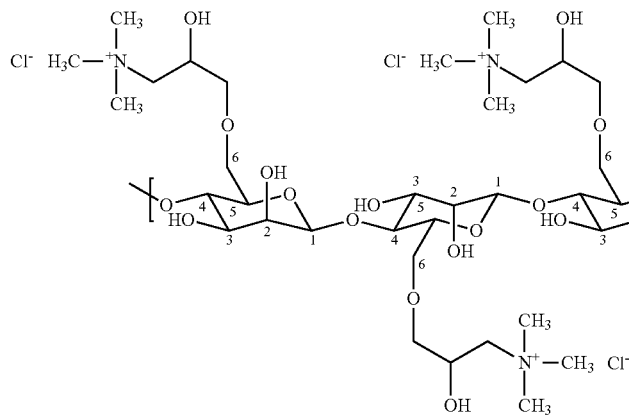
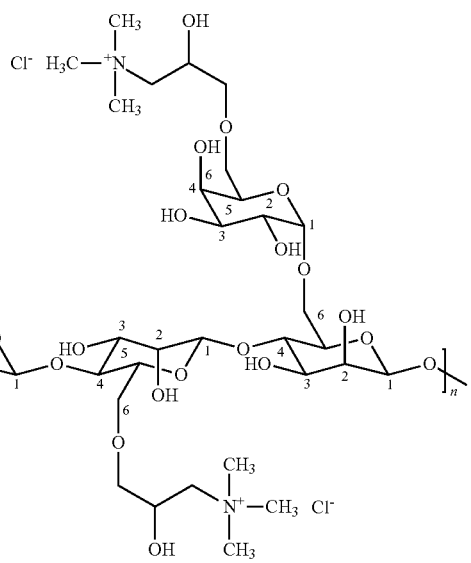

In the schematic representation above, the C-6 hydroxyl groups on the polymer are shown to be fully functionalized in this embodiment. In other embodiments of the invention, some but not all of the C-6 hydroxyl groups can be cationically functionalized. In still other embodiments, one or more of the C-2 and/or one or more of the C-3 hydroxyl groups on the mannosyl and galactosyl units and/or one or more of the C-4 hydroxyl groups on the galactosyl units of the polymer can be cationically functionalized.

Chemical modification of *Cassia* gum leads to incorporation of the cationic moiety, onto the backbone. The chemical modification leads to various physical property changes. For instance, cationic *Cassia* polymers exhibit cold water or improved cold water solubility. It is able to hydrate in cold water and build viscosity by forming a colloidal thixotopic dispersion in cold water.

In a given composition or application, the cationic *Cassia* polymers of this invention can, but need not, serve more than one function, such as a fixative, thickener, skin and hair conditioner, film former and carrier or deposition aid. In a fixative composition the amount of cationic *Cassia* polymer that can be employed depends upon the purpose for which they are included in the formulation and can be determined by person skilled in the hair fixative formulation art. Thus, as long as the desired physicochemical and functional properties are achieved, a useful amount of cationic *Cassia* polymer on a total composition weight basis, typically can vary in the range of from about 0.01% to about 25% in one aspect of the invention, from about 0.1 wt. % to about 10 wt. % in another aspect, and from about 0.2 wt. % to about 5 wt. % in a further aspect of the invention, based on the total weight of the composition, but is not limited thereto.

In addition to its fixative properties, the cationic *Cassia* polymers of the invention can be employed as conditioners and/or deposition aids in hair fixative and styling shampoo compositions. The cationic *Cassia* polymer can be used in shampoos and conditioners to facilitate combability. The positively charged nitrogen atom interacts with the negatively charged hair fibers to form films. They also make the hair feel softer and smoother to the touch without creating excessive residual build-up. Cationic *Cassia* polymers can be used as part of a conditioner package in a conditioning detergent formulation that not only imparts cleansing, wet detangling, dry detangling and manageability properties to the hair, but also is relatively non-irritating. This composition is thus suitable for use by young children and adults having sensitive skin and eyes. In addition, cationic *Cassia* has been found to be an excellent deposition aid in the deposition of conditioning and therapeutic agents to the hair.

In styling shampoo, the use of the cationic *Cassia* polymers of the present invention as deposition aids to enhance the deposition of water-insoluble styling polymers improves the styling performance (conditioning, curl retention, superior hair feel) of the hair. The cationic *Cassia* polymers of the invention can be used as deposition aids in combination with water-insoluble hair styling polymers selected from the group of (meth)acrylates copolymers and silicone-grafted (meth)acrylates. Examples include t-butylacrylate/2-ethylhexylacrylate copolymers, t-butylacrylate/2-ethylhexylmethacrylate copolymers, t-butyl acrylate/2-ethylhexyl methacrylate/polydimethylsiloxane macromer, and t-butyl methacrylate/2-ethylhexylmethacrylate/polydimethylsiloxane macromer copolymers, and mixtures thereof.

Hair fixative product formulations comprising the cationic *Cassia* polymers of the invention can contain various additives and cosmetic adjuvants, conventionally or popularly included in hair fixative compositions, as are well known in the art. In one embodiment of the invention the cationic *Cassia* fixative polymers of the invention can be formulated in combination with derivatized and non-derivatized hydrocolloids derived from natural sources such as, for example, polysaccharides obtained from tree, shrub, and fruit exudates, such as gum arabic, gum gahatti, and gum tragacanth, and pectin; seaweed extracts, such as alginates and carrageenans; algae extracts, such as agar; microorganism produced polysaccharides, such as xanthan, gellan, and wellan gums; cellulose ethers, such as ethylhexylethylcellulose (EHEC), hydroxybutylmethylcellulose (HBMC), hydroxyethylmethylcellulose (NEMC), hydroxypropylmethylcellulose (HPMC), methyl cellulose (MC), carboxymethylcellulose (CMC), hydroxyethylcellulose (HEC), hydroxypropylcellulose (HPC) and cetyl hydroxyethylcellulose; polygalactomannan gums selected from fenugreek, *Cassia*, locust bean, tara and guar; and mixtures thereof.

By derivatized hydrocolloid is meant that the above mentioned hydrocolloids can be derivatized with a functionalization agent reactive with a functional group, e.g., a hydroxyl group, contained on the hydrocolloid backbone. For example, derivatives of the cellulose ethers containing quaternary ammonium groups can be made by reacting a cellulose ether, e.g., hydroxyethylcellulose, with an epoxide substituted by a trialkyl ammonium salt group, e.g., glycidyltrimethylammonium chloride, to give the quaternary substituted cellulose.

Derivatized hydrocolloids can be made by grafting a cellulose ether such as hydroxymethylcellulose, hydroxyethylcellulose or hydroxypropylcellulose with a free radically polymerizable, ethylenically unsaturated quaternary ammonium salts such as N,N,N-trimethylaminoethyl methacrylate methyl sulfate or halide, 2-hydroxy-3-methacryloxypropyl trimethyl ammonium methyl sulfate or halide, vinyl benzyl trialkyl ammonium methyl sulfate or halide, dialkyl diallyl ammonium methyl sulfate or halide; sodium or ammonium styrene sulfonate. Such polymers are described in U.S. Pat. No. 4,131,576.

Derivatized hydrocolloids can also be made by quaternizing a polygalactomannan such as locust bean gum or guar with a quaternizing agent. Quaternized polygalactomannans can be made by reacting guar gum with a haloalkyl substituted quaternary ammonium compound, e.g., 4-chloro-2-butenyl trimethylammonium chloride. A process for producing derivatized polygalactomannan gums is described in U.S. Pat. No. 4,031,307.

When the above mentioned hydrocolloids are formulated into the fixative composition of the present invention the weight ratio of cationic *Cassia* fixative to hydrocolloid(s) range from about 1:10 to about 10:1 in one aspect, from about 2:8 to about 8:2 in another aspect, from about 2.5:7.5 to about 7.5:2.5 in a further aspect, from about 1:5 to about 5:1 in another aspect, and from about 1:2 to about 2:1 in a still further aspect.

Surprisingly, it was discovered that the blends of cationic *Cassia* and non-derivatized guar gum provide an unexpected synergy in rheology and fixative properties. Mechanical blends of cationic *Cassia* and guar achieve superior viscosity and yield values when compared to the sum of the individual viscosity and yield values for cationic *Cassia* and guar. The same effect was noted for curl retention and hair stiffness values. An optimum synergistic effect for rheology and fixative properties was noted at cationic *Cassia* to guar weight ratios of from about 1:1 to about 2:1.

For the individual galactomannan hydrocolloids optimum fixative properties can be achieved if the ratio of cationic *Cassia* polymers of the invention to the above described polysaccharides on a wt. to wt. basis is between about 9:1 and about 1:9 in one aspect, between about 8:2 and 2:8 in another aspect, between about 6:4 and 4:6 in a further aspect, between about 2:1 to 1:2 is still further aspect, and 1:1 in another aspect.

In another embodiment of the invention the cationic *Cassia* fixative polymers of the invention can be formulated in combination with one or more auxiliary rheology modifiers. Suitable rheology modifiers include synthetic and semi-synthetic rheology modifiers. Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule wherein the substituent is preferably and independently selected from $C_{1-4}$ alkyl, —CN, and —COON. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. Nos. 5,087,445; 4,509,949; and 2,798,053 herein incorporated by reference.

In one embodiment the AST rheology modifier is a crosslinked homopolymer polymerized from acrylic acid or methacrylic acid and is generally referred to under the INCI name of Carbomer. Commercially available Carbomers include Carbopol® polymers 934, 940, 941, 956, 980 and 996 available from Lubrizol Advanced Materials, Inc. In another embodiment the AST rheology modifier is selected from a crosslinked copolymer polymerized from a first monomer selected from one or more monomers of (meth)acrylic acid, substituted acrylic acid, and salts of (meth)acrylic acid and substituted acrylic acid and a second monomer selected from one or more $C_1$-$C_5$ alkyl acrylate esters of (meth)acrylic acid. These polymers are designated under the INCI name of Acrylates Copolymer. Acrylates Copolymers are commercially available under the trade names Aculyn® 33 from Rohm and Haas and Carbopol® Aqua SF-1 from Lubrizol Advanced Materials, Inc. In a further aspect the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect the monomers can be polymerized in the presence of a steric stabilizer such as disclosed in U.S. Pat. No. 5,288,814 which is herein incorporated by reference. Some of the forgoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc. Any vinyl or acrylic based rheology modifiers are suitable.

Another class of synthetic rheology modifiers suitable for use in the present invention includes hydrophobically modified ASTs commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect associative monomers can be prepared by the condensation (e.g., esterification or etherification) of a polyethoxylated and/or polypropoxylated aliphatic alcohol. (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., $\alpha,\alpha$-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, isaooctyl alcohol (2-ethyl hexanol), pelargonic alcohol (1-nonanol), decyl alcohol, lauryl alcohol, myristyl alcohol, cetyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843 which are herein incorporated by reference. In addition, an extensive review of HASE polymers is found in Gregory D. Shay, Chapter 25, "Alkali-Swellable and Alkali-Soluble Thickener Technology A Review", *Polymers in Aqueous Media—Performance Through Association*, Advances in Chemistry Series 223, J. Edward Glass (ed.), ACS, pp. 457-494, Division Polymeric Materials, Washington, D.C. (1989), the relevant disclosures of which are incorporated herein by reference. The HASE polymers are commercially available from Rohm & Haas under the trade designations Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer).

Another class of synthetic and semi-synthetic rheology modifiers suitable for use in the present invention includes cationically modified acrylic polymers and copolymers and cationically modified cellulose ethers. The acrylic polymers and copolymers and cellulose ethers are cationically modified via quaternization. For the acrylic polymers and copolymers, quaternization can occur by polymerizing a quaternized monomer into the acrylic polymer backbone or by post functionalizing the acrylic polymer with a quaternizing agent. An exemplary quaternary acrylic polymer is designated under INCI nomenclature as Polyquaternium-37 and is commercially available under the trade names Synthalen CR21 and Synthalen CN, from 3V Inc. The quaternized celluloses are prepared by post functionalizing the desired cellulosic backbone (e.g., hydroxyethyl cellulose) with a quaternizing agent such as a quaternary ammonium salt (e.g, diallyldimethyl ammonium chloride, trimethyl ammonium chloride substituted epoxide). Exemplary quaternary cellulosic polymers are designated under the INCI names Polyquaternium-4, Polyquaternium-10, and Polyquaternium-67.

In another embodiment, acid swellable associative polymers can be used with the cationic fixatives of the present invention. Such polymers generally have cationic and associative characteristics. These polymers are free radical addition polymers polymerized from a monomer mixture comprising an acid sensitive amino substituted hydrophilic monomer (e.g., dialkylamino alkyl(meth)acrylates or (meth) acrylamides), an associative monomer (defined hereinabove), a lower alkyl(meth)acrylate or other free radically polymerizable comonomers selected from hydroxyalkyl esters of (meth)acrylic acid, vinyl and/or allyl ethers of polyethylene glycol, vinyl and/or allyl ethers of polypropylene glycol, vinyl and/or allyl ethers of polyethylene glycol/polypropylene glycol, polyethylene glycol esters of (meth)acrylic acid, polypropylene glycol esters of (meth)acrylic acid, polyethylene glycol/polypropylene glycol esters of (meth)acrylic acid), and combinations thereof. These polymers can optionally be crosslinked. By acid sensitive is meant that the amino substituent becomes cationic at low pH values, typically ranging from about 0.5 to about 6.5. Exemplary acid swellable associative polymers are commercially available under the trade name Structure® Plus (INCI Name: Acrylates/Aminoacrylates/C10-C30 Alkyl PEG-20 Itaconate) from National Starch and Chemical Company, and Carbopol® Aqua CC (INCI Name: Polyacrylates-1 Crosspolymer) from Lubrizol Advanced Materials, Inc. In one aspect the acid swellable polymer is a copolymer of one or more $C_1$-$C_5$ alkyl esters of (meth)acrylic acid, $C_1$-$C_4$ dialkylamino $C_1$-$C_6$ alkyl methacrylate, PEG/PPG-30/5 allyl ether, PEG 20-25 $C_{10}$-$C_{30}$ alkyl ether methacrylate, hydroxy $C_2$-$C_6$ alkyl methacrylate crosslinked with ethylene glycol dimethacrylate. Other useful acid swellable associative polymers are disclosed in U.S. Pat. No. 7,378,479, the disclosure of which is herein incorporated by reference.

Hydrophobically modified alkoxylated methyl glucoside, such as, for example, PEG-120 Methyl Glucose Dioleate, PEG-120 Methyl Glucose Trioleate, and PEG-20 Methyl Glucose Sesquistearate, available from Lubrizol Advanced Materials, Inc., under the trade names, Glucamate® DOE-120, Glucamate™ LT, and Glucamate™ SSE-20, respectively, are also suitable rheology modifiers.

Other rheology modifiers suitable for use in the fixative compositions of the invention are disclosed in U.S. Pat. No. 7,205,271 the disclosure of which is herein incorporated by reference.

The rheology modifiers set forth above, when employed, can be used alone or in combination and typically are used in an amount ranging from about 0.1 wt. % to about 5 wt. % in one aspect, from about 0.3 wt. % to about 3 wt. % in another aspect, and from about 0.5 wt. % to about 2 wt. % in further aspect, based on the total weight of the fixative compositions of the present invention.

In another embodiment of the invention the cationic *Cassia* fixative polymers of the invention can be formulated in combination with an auxiliary fixative(s). Suitable optional auxiliary hair fixative polymers include natural and synthetic polymers such as, for example, polyacrylates, polyvinyls, polyesters, polyurethanes, polyamides, modified cellulose, starches, and mixtures thereof. These polymers can be nonionic, anionic, cationic and amphoteric in nature and include without limitation one or more of polyoxythylenated vinyl acetate/crotonic acid copolymers, vinyl acetate crotonic acid copolymers, vinyl methacrylate copolymers, monoalkyl esters of poly(methyl vinyl ether (PVM)/maleic acid (MA)), such as, for example, ethyl, butyl and isopropyl esters of PVM/MA copolymer acrylic acid/ethyl acrylate/N-tert-butyl-acrylamide terpolymers, and poly (methacrylic acid/acrylamidomethyl propane sulfonic acid), acrylates copolymer, octylacrylamide/acrylates/butylaminoethyl methacrylate copolymer, acrylates/octylacrylamide copolymer, vinyl acetate (VA)/crotonates/vinyl neodeanoate copolymer, poly (N-vinyl acetamide), poly(N-vinyl formamide), corn starch modified, sodium polystyrene sulfonate, polyquaterniums such as, for example, Polyquaternium-4, Polyquaternium-11, Polyquaternium-24, Polyquaternium-28, Polyquaternium-29, Polyquaternium-32, Polyquaternium-34, Polyquaternium-37, Polyquaternium-39, Polyquaternium-44, Polyquaternium-46, Polyquaternium-47, Polyquarternium-55, Polyquaternium-69, Polyquaternium-87, polyether-1, polyurethanes, VA/acrylates/lauryl methacrylate copolymer, adipic acid/dimethylaminohydroxypropyl diethylene AMP/acrylates copolymer, methacrylol ethyl betaine/acrylates copolymer, polyvinylpyrrolidone (PVP), vinyl pyrrolidone (VP)/dimethylaminoethylmethacrylate copolymer, VP/methacrylamide/vinyl imidazole copolymer, VP/dimethylaminopropylamine (DMAPA) acrylates copolymer, VP/vinylcaprolactam/DMAPA acrylates copolymer, VP/dimethylaminoethylmethacrylate copolymer, VP/DMAPA acrylates copolymer, vinyl caprolactam/VP/dimethylaminoethyl methacrylate copolymer, VA/butyl maleate/isobornyl acrylate copolymer, VA/crotonates copolymer, acrylate/acrylamide copolymer, VA/crotonates/vinyl propionate copolymer, VP/vinyl acetate/vinyl propionate terpolymers, VA/crotonates, VP/vinyl acetate copolymer, VP/acrylates copolymer, VA/crotonic acid/vinyl proprionate, acrylates/acrylamide, acrylates/octylacrylamide, acrylates/hydroxyacrylates copolymer, acrylates/hydroxyesteracrylates copolymer, acrylates/stereth-20 methacrylate copolymer, tert-butyl acrylate/acrylic acid copolymer, diglycol/cyclohexanedimethanol/isophthalates/sulfoisophthalates copolymer, VA/butyl maleate and isobornyl acrylate copolymer, vinylcaprolactam/VP/dimethylaminoethyl methacrylate, VA/alkylmaleate half ester/N-substituted acrylamide terpolymers, vinyl caprolactam/VP/methacryloamidopropyl trimethylammonium chloride terpolymer, methacrylates/acrylates copolymer/amine salt, polyvinylcaprolactam, polyurethanes, hydroxypropyl guar, poly (methacrylic acid/acrylamidomethyl propane sulfonic acid (AMPSA), ethylenecarboxamide (EC)/AMPSA/methacrylic acid (MAA), poylurethane/acrylate copolymers and hydroxypropyl trimmonium chloride guar, acrylates copolymer, acrylates crosspolymer, AMP-acrylates/allyl methacrylate copolymer, polyacrylate-14, polyacrylate-2 crosspolymer, octylacrylamide/acrylates/butylaminoethyl methacrylate copolymer, acrylates/octylacrylamide copolymer, VA/crotonates/vinyl neodeanoate copolymer, poly(N-vinyl acetamide), poly(N-vinyl formamide), polyurethane, acrylates/lauryl acrylate/stearyl acrylate/ethylamine oxide methacrylate copolymer, methacryloyl ethyl betaines/methacrylates copolymer, corn starch modified, sodium polystyrene sulfonate, polyurethane/acrylates copolymer, pyrrolidone carboxylic acid salt of chitosan, chitosan glycolate, cationic polygalactomannans, such as, for example, quaternized derivatives of guar, such as, for example, guar hydroxypropyl trimmonium chloride and hydroxypropyl guar hydroxypropyl trimmonium chloride. Many of the foregoing polymers are referred to by their INCI nomenclature set forth in the *International Cosmetic Ingredient Dictionary* published by the Cosmetic, Toiletry, and Fragrance Association, Washington D.C. Other suitable auxiliary fixative polymers are disclosed in U.S. Pat. No. 7,205,271, the disclosure of which is herein incorporated by reference.

The fixative polymer, alone or in combination with the optional auxiliary fixative(s), typically comprises about 0.01 wt. % to about 25 wt. % in one aspect, from about 0.1 wt. % to about 10 wt. % in another aspect, and about 0.2 wt. % to about 5 wt. % in a further aspect of the total weight of the fixative composition. The optional fixative polymer can be present in the amount of from 0 wt. % to about 24.99 wt. % of the total fixative composition.

One or more cosmetically acceptable adjuvants and additives can be included in the hair fixative compositions of the invention. Such adjuvants and additives include but are not limited to pH adjusting agents or buffering agents, emulsifiers, emollients, surfactants, conditioning agents, and mixtures thereof.

The pH adjusting agent is utilized in any amount necessary to obtain a desired pH value in the fixative composition. In one aspect, the fixative composition of the invention can contain at least one alkalizing (alkaline pH adjusting agent) or acidifying agent (acidic pH adjusting agent) in amounts from 0.01 to 30 wt. % of the total weight of the composition. Non-limiting examples of alkaline pH adjusting agents include ammonia, alkali metal hydroxides, such as sodium hydroxide, and potassium hydroxide; ammonium hydroxide, alkanolamines such as mono-, di- and triethanolamine; diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis (hydroxypropyl)ethylenediamine; and alkali metal salts of inorganic acids, such as sodium borate (borax), sodium phosphate, sodium pyrophosphate, and the like, and mixtures thereof. Non-limiting examples of acidic pH adjusting agents include organic acids, such as citric acid, acetic acid, alpha-hydroxy acid, beta-hydroxy acid, salicylic acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

The emulsifier can be selected from a water-in-oil emulsifier, an oil-in-water emulsifier, and mixtures thereof. In one aspect of the invention the emulsifier can be present in an amount ranging from about 0.5 wt. % to about 12 wt. %, from about 1 wt. % to about 15 wt. % in another aspect, and from about 5 wt. % to about 10 wt. % in a further aspect, based on the total weight of the fixative composition.

Exemplary emulsifiers include but are not limited to $C_{12}$-$C_{18}$ fatty alcohols; alkoxylated $C_{12}$-$C_{18}$ fatty alcohols; $C_{12}$-$C_{18}$ fatty acids; and alkoxylated $C_{12}$-$C_{18}$ fatty acids, the alkoxylates each having 10 to 30 units of ethylene oxide, propylene oxide, and combinations of ethylene oxide/propylene oxide; $C_8$-$C_{22}$ alkyl mono- and oligoglycosides; ethoxylated sterols; partial esters of polyglycerols; esters and partial esters of polyols having 2 to 6 carbon atoms and saturated and unsaturated fatty acids having 12 to 30 carbon atoms; partial esters of polyglycerols; and organosiloxanes; and combinations thereof.

The fatty alcohols, acids and alkoxylated fatty alcohols and fatty acids are as described in the emollient description above. In one aspect of the invention the fatty alcohols and fatty acids each are ethoxylated with 10 to 30 units of ethylene oxide.

The $C_8$-$C_{22}$ alkyl mono- and oligoglycoside emulsifiers are prepared by reacting glucose or an oligosaccharide with primary fatty alcohols having 8 to 22 carbon atoms. Products which are obtainable under the trademark Plantacare® comprise a glucosidically bonded $C_8$-$C_{16}$ alkyl group on an oligoglucoside residue whose average degree of oligomerization is 1 to 2. Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Exemplary ethoxylated sterols include ethoxylated vegetable oil sterols such as, for example, soya sterols. The degree of ethoxylation is greater than about 5 in one aspect, and at least about 10 in another aspect. Suitable ethoxylated sterols are PEG-10 Soy Sterol, PEG-16 Soy Sterol and PEG-25 Soy Sterol.

The partial esters of polyglycerols have 2 to 10 glycerol units and are esterified with 1 to 4 saturated or unsaturated, linear or branched, optionally hydroxylated $C_8$-$C_{30}$ fatty acid residues. Representative partial esters of polyglycerols include diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

The saturated $C_{12}$-$C_{30}$ fatty alcohol emulsifiers are as described in the emollient description set forth above. In one aspect of the invention, the fatty alcohol emulsifier is selected from but not limited to cetyl alcohol, stearyl alcohol, arachidyl alcohol, behenyl alcohol and lanolin alcohol or mixtures of these alcohols, and as are obtainable in the hydrogenation of unsaturated vegetable oil and animal fatty acids.

Emulsifiers based on the esters and partial esters of polyols having 2 to 6 carbon atoms and linear saturated and unsaturated fatty acids having 12 to 30 carbon atoms are, for example, the monoesters and diesters of glycerol or ethylene glycol or the monoesters of propylene glycol with saturated and unsaturated $C_{12}$ to $C_{30}$ fatty acids.

The partially esterified polyglycerol emulsifiers include 2 to about 10 glycerol units and esterified with 1 to 5 saturated or unsaturated, linear or branched, optionally hydroxylated $C_8$ to $C_{30}$ fatty acid residues.

The organosiloxane emulsifiers are polymeric emulsifiers that contain at least one hydrophobic portion and at least one hydrophilic portion. The polymer backbone contains repeating siloxy units that can have cyclic, linear or branched repeating units, e.g. di($C_1$-$C_5$)alkylsiloxy units, typically dimethylsiloxy units.

The hydrophilic portion of the organosiloxane is generally achieved by substitution onto the polymeric backbone of a residue that confers hydrophilic properties to a portion of the molecule. The hydrophilic residue may be substituted on a terminus of the polymeric organosiloxane, or on any one or more repeating units of the polymer. Generally, the hydrophilic residue is derived from ethylene oxide units that are grafted onto the polymer backbone. In general, the repeating dimethylsiloxy units of modified polydimethylsiloxane emulsifiers are hydrophobic in nature due to the methyl groups, and confer the hydrophobicity properties to the molecule. In addition, longer chain alkyl residues, hydroxy terminated polypropyleneoxy residues, hydroxy terminated polyether residues comprising a combination of ethylene oxide and propylene oxide residues, and/or other types of residues can be substituted onto the siloxy backbone to confer additional emulsification properties to the backbone. Polyether substituted organosiloxane emulsifiers are known as dimethicone copolyols and are widely commercially available. The dimethicone polyols can be random or block copolymers. A generally useful class of dimethicone polyols is block copolymers having blocks of polydimethylsiloxane and blocks of polyalkylene oxide, such as blocks of polyethylene oxide, polypropylene oxide, or both.

Dimethicone copolyols are disclosed in U.S. Pat. Nos. 5,136,063 and 5,180,843, the disclosures of which are incorporated herein by reference. In addition, dimethicone copolyols are commercially available under the Silsoft® and Silwet® brand names from the General Electric Company (GE-OSi). Specific product designations include but are not limited to Silsoft 305, 430, 475, 810, 895, Silwet L 7604 (GE-OSi); Dow Corning® 5103 and 5329 from Dow Corning Corporation; and Abil® dimethicone copolyols, such as, for example WE 09, WS 08, EM 90 and EM 97 from Degussa Goldschmidt Corporation; and Silsense™ dimethicone copolyols, such as Silsense Copolyol-1 and Silsense Copolyol-7, available from Lubrizol Advanced Materials, Inc.

Blends of dimethicone copolyols in cyclomethicone fluids are also useful emulsifiers in the present invention. An exemplary dimethicone/cyclomethicone blend is commercially available as Dow Corning® 5225 C and is a 10 wt. % dispersion of PEG/PPG-18/18 Dimethicone in cyclopentasiloxane fluid available from Dow Corning Corporation.

Suitable emollients include but are not limited to an emollient selected from silicone fluids (e.g., volatile silicone oils and non-volatile silicone oils); mineral oils; petrolatums; vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); and polyalkylene glycols; lanolin and lanolin derivatives; and the like. The emollient can be used alone or in combination with one or more emollients of the present invention. The emollient(s) can be utilized in an amount ranging from about 0.5 wt. % to about 30 wt. % by weight of the total fixative composition in one aspect 0.1 wt. % to 25 wt. % in another aspect, and 5 wt. % to 20 wt. % in a further aspect.

Volatile silicone oils include cyclic and linear polydimethylsiloxanes, low molecular weight organo-functional silicones, and the like. Cyclic volatile silicones(cyclomethicones) typically contain about 3 to about 7 silicon atoms, alternating with oxygen atoms, in a cyclic ring structure. Each silicon atom is typically substituted with two alkyl groups, such as, for example, methyl groups. Volatile linear polydimethylsiloxanes(dimethicones) typically contain about 2 to about 9 silicon atoms, alternating with oxygen atoms in a linear arrangement. Each silicon atom is also substituted with two alkyl groups (the terminal silicon atoms are substituted with three alkyl groups), such as, for example, methyl groups. The linear volatile silicones typically have viscosities of less than about 5 cP at 25° C., while the cyclic volatile silicones typically have viscosities of less than about 10 cP at 25° C. "Volatile" means that the silicone has a measurable vapor pressure, or a vapor pressure of at least 2 mm of Hg at 20° C. Non-volatile silicones have a vapor pressure of less than 2 mm Hg at 20° C. A description of volatile silicones is found in Todd and Byers, "Volatile Silicone Fluids for Cosmetics", *Cosmetics and Toiletries*, Vol. 91(1), pp. 27-32 (1976), and in Kasprzak, "Volatile Silicones", *Soap/Cosmetics/Chemical Specialties*, pp. 40-43 (December 1986), each incorporated herein by reference.

Exemplary volatile cyclomethicones are D4 cyclomethicone(octamethylcyclotetrasiloxane), D5 cyclomethicone(decamethylcyclopentasiloxane), D6 cyclomethicone, and blends thereof (e.g., D4/D5 and D5/D6). Volatile cyclomethicones and cyclomethicone blends are commercially available from G.E. Silicones as SF1173, SF1202, SF1256, and SF1258, Dow Corning Corporation as Dow Corning® 244, 245, 246, 345, and 1401 Fluids. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning Corporation as Dow Corning 200® Fluid (e.g., product designations 0.65 CST, 1 CST, 1.5 CST, and 2 CST) and Dow Corning® 2-1184 Fluid.

Exemplary volatile low molecular weight organo-functional silicones include phenyl trimethicone, caprylyl trimethicone, caprylyl methicone, and hexyl methicone, and blends thereof. Low molecular weight organo-functional silicones are commercially available from Clariant under the trade name Silcare® 41M10, Slcare® 31 M60, Silcare® 41M10, and Silcare® 41M15.

The non-volatile silicone oils useful as emollients in the present invention are linear and typically have viscosities of from about 10 cP to about 100,000 cP at 25° C. They typically contain above about 10 dialkyl/diaryl or monoalkyl/monoaryl substituted silicon atoms, alternating with oxygen atoms in a linear arrangement. They include polyalkylsiloxane, polyarylsiloxane, and polyalkylarylsiloxane polymers. Exemplary non-volatile silicone oils include the polydimethylsiloxanes (dimethicones), polydiethylsiloxanes, polymethylphenylsiloxanes, and the like. In one aspect of the invention, the non-volatile silicone oil is selected from a non-volatile polydimethylsiloxane having a viscosity range from about 10 cP to about 100,000 cP at 25° C. Non-volatile dimethicones are commercially available from Dow Corning Corporation as Dow Corning 200® Fluid (product designations 10 CST through 10,000 CST).

Mineral oils and petrolatums include cosmetic, USP and NF grades and are commercially available from Penreco under the Drakeol® and Penreco® trade names. Mineral oil includes hexadecane and paraffin oil.

Exemplary vegetable oils suitable an emollient component in the present invention include but are not limited to peanut oil, sesame oil, avocado oil, coconut oil, cocoa butter, almond oil, safflower oil, corn oil, cotton seed oil, sesame seed oil, walnut oil, castor oil, olive oil, jojoba oil, palm oil, palm kernel oil, soybean oil, wheat germ oil, linseed oil, sunflower seed oil; and the mono-, di-, and triglycerides thereof. Exemplary mono-, di- and triglycerides are, for example, caprylic triglyceride, capric triglyceride, caprylic/capric triglyceride, and caprylic/capric/lauric triglyceride, caprylic/capric/stearic triglyceride, and caprylic/capric/linoleic triglyceride.

Ethoxylated mono- and diglycerides are also suitable as an emollient component of the present invention, such as, for example, PEG-8 Caprylic/Capric Glycerides.

Suitable fatty alcohol emollients include but are not limited to fatty alcohols containing 8 to 30 carbon atoms. Exemplary fatty alcohols include capryl alcohol, pelargonic alcohol, capric alcohol, lauryl alcohol, myristyl alcohol, cetyl alcohol, isocetyl alcohol, stearyl alchohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acid emollients include but are not limited to fatty acids containing 10 to 30 carbon atoms. Exemplary fatty acids are selected from capric acid, lauric acid, myristic acid, palmitic acid, stearic acid, oleic acid, linoleic acid, arachidic acid, behenic acid, and mixtures thereof.

Suitable fatty acid and fatty alcohol ester emollients include but are not limited to hexyl laurate, decyl oleate, isopropyl stearate, isopropyl isostearate, butyl stearate, octyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl heopentanoate, diisopropyl sebacate, isostearyl lactate, lauryl lactate, diethyl hexyl maleate, PPG-14 butyl ether and PPG-2 myristyl ether propionate, cetearyl octanoate, and mixtures thereof.

Alkoxylated fatty alcohols are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect of the invention, the ethoxylated fatty alcohols can be represented by the formula R—$(OCH_2CH_2)_n$—OH, wherein R represents the aliphatic residue of the parent fatty alcohol and n represents the number of molecules of ethylene oxide. In another aspect of the invention, R is derived from a fatty alcohol containing 8 to 30 carbon atoms. In one aspect, n is an integer ranging from 2 to 50, 3 to 25 in another aspect, and 3 to 10 in a further aspect. In a still further aspect, R is derived from a fatty alcohol emollient set forth above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and mixed ethoxylated/propoxylated adducts of the foregoing fatty alcohols are also contemplated within the scope of the invention. The ethylene oxide and propylene oxide units of the ethoxylated/propoxylated fatty alcohols can be arranged in random or in blocky order.

More specific examples of ethoxylated alcohols are but are not limited to Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 pareth 3-8, C11-15 pareth 5-40, C11-21 Pareth 3-10, C12-13 pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10.

Specific examples of propoxylated alcohols are but are not limited to PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols are but are not limited to PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 C9-15 Pareth-6, PPG-6 C9-11 Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradaeeth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Laureth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Alkoxylated fatty acids are formed when a fatty acid is reacted with an alkylene oxide or with a pre-formed polymeric ether. The resulting product may be a monoester, diester, or mixture thereof. Suitable ethoxylated fatty acid ester emollients suitable for use in the present invention are products of the addition of ethylene oxide to fatty acids. The product is a polyethylene oxide ester of a fatty acid. In one aspect of the invention, the ethoxylated fatty acid esters can be represented by the formula R—C(O)O(CH$_2$CH$_2$O)$_n$—H, wherein R represents the aliphatic residue of a fatty acid and n represents the number of molecules of . ethylene oxide. In another aspect, n is an integer ranging from 2 to 50, 3 to 25 in another aspect, and 3 to 10 in a further aspect. In still another aspect of the invention, R is derived from a fatty acid containing 8 to 24 carbon atoms. In a still further aspect, R is derived from a fatty acid emollient set forth above. It is to be recognized that propoxylated and ethoxylated/propoxylated products of the foregoing fatty acids are also contemplated within the scope of the invention. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG-dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Guerbet ester emollients are formed from the esterification reaction of a Guerbet alcohol with a carboxylic acid. Guerbet ester emollients are commercially available from the Noveon Consumer Specialties Division of Lubrizol Advanced Materials, Inc. under product designations G-20, G-36, G-38, and G-66.

Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from the Noveon Consumer Specialties Division of Lubrizol Advance Materials, Inc. under the trade names Lanolin LP 108 USP, Lanolin USP AAA, Acetulan™, Ceralan™ Lanocerin™, Lanogel™ (product designations 21 and 41), Lanogene™, Modulan™, Ohlan™, Solulan™ (product designations 16, 75, L-575, 98, and C-24), Vilvanolin™ (product designations C, CAB, L-101, and P).

Surfactants are generally employed as cleansing agents, emulsifying agents, stabilizers, foam boosters, structurants, hydrotropes and suspending agents. While amounts of the surfactant if employed can vary widely, the amounts which are often utilized generally range from about 1 wt. % to about 80 wt. % of the in one aspect, from about 5 wt. % to about 65 wt. % in another aspect, from about 6 wt. % to about 30 wt. % in a further aspect, and from about 8 wt. % to about 20 wt. % in a still further aspect of the invention, based based upon the total weight of the fixative composition. The surfactant can be selected from any class of surfactants, i.e., anionic surfactants, cationic surfactants, nonionic surfactants, amphoteric surfactants, and mixtures thereof. The term "amphoteric surfactant" as used herein includes zwitterionic surfactants. In-depth discussions of the various classes of surfactants are contained in the Cosmetics & Toiletries® C&T Ingredient Resource Series, "Surfactant Encyclopedia", 2nd Edition, Rieger (ed), Allured Publishing Corporation (1996); Schwartz, et al., Surface Active Agents, Their Chemistry and Technology, published 1949; and Surface Active Agents and Detergents, Volume II, published 1958, Interscience Publishers; each incorporated herein by reference.

Anionic surfactants include substances having a negatively charged hydrophobe or that carry a negative charge when the pH is elevated to neutrality or above, such as acylamino acids, and salts thereof, for example, acylglutamates, acyl peptides, sarcosinates, and taurates; carboxylic acids, and salts thereof, for example, alkanolic acids and alkanoates, ester carboxylic acids, and ether carboxylic acids; phosphoric acid ester and salts thereof; sulfonic acids and salts thereof, for example, acyl isethionates, alkylaryl sulfonates, alkyl sulfonates, and sulfosuccinates; and sulfuric acid esters, such as alkyl ether sulfates and alkyl sulfates.

Non-limiting examples of anionic surfactants include mono-basic salts of acylglutamates that are slightly acidic in aqueous solution, such as sodium acylglutamate and sodium hydrogenated tallow glutamate.; salts of acyl-hydrolyzed protein, such as potassium, palmitoyl hydrolyzed milk protein, sodium cocoyl hydrolyzed soy protein, and TEA-abietoyl hydrolyzed collagen; salts of acyl sarcosinates, such as ammonium myristoyl sarcosine, sodium cocoyl sarcosinate, and TEA-lauroyl sarcosinate; salts of sodium methyl acyltaurates, such as sodium lauroyl taurate, sodium methyl oleyl taurate and sodium methyl cocoyl taurate; alkanoic acids and alkanoates, such as fatty acids derived from animal and vegetable glycerides that form water-soluble soaps and water-insoluble emulsifying soaps, including sodium stearate, ammonium stearate, aluminum stearate, and zinc undecylenate; ester carboxylic acids, such as dinonoxynol-9-citrate; salts of acyl lactylates such as calcium stearoyl lactylate and laureth-6 citrate; ethercarboxylic acids derived from ethyoxylated alcohols or phenols having varying lengths of polyoxyethylene chains, such as nonoxynol-8 carboxylic acid, and sodium trideceth-13 carboxylate; mono- and di-esters of phosphoric acid and their salts, such as phospholipids, dilaureth-4-phosphate, DEA-oleth-10 phosphate and triethanolamine lauryl phosphate; salts of acylisethionate, such as sodium cocoyl isethionate; alkylarylbenzene sulfonates, such as alpha-olefin sulfonates (AOS) and alkali metal, alkaline earth metal, and alkanolamine salts thereof, and sodium dodecylbenzene sulfonate; alkyl sulfonates, such as sodium $C_{12}$ to $C_{14}$ olefin sulfonate, sodium $C_{14}$ to $C_{16}$ olefin sulfonate, sodium cocomonoglyceride sulfonate, sodium $C_{12}$ to $C_{15}$ pareth-15 sulfonate, and sodium lauryl sulfoacetate; sulfosuccinates, such as mono- and di-esters of sulfosuccinic acid, salts thereof and alkoxylated alkyl and alkylamido derivatives thereof, such as di-$C_4$ to $C_{10}$ alkyl sodium sulfosuccinate, disodium laureth sulfosuccinate, disodium oleamido MEA-sulfosuccinate, and disodium $C_{12}$ to $C_{15}$ pareth sulfosuccinate; alkyl ether sulfates, such as sodium and ammonium lauryl ether sulfate (having about 1 to about 12 moles ethylene oxide), e.g., sodium laureth sulfate; alkyl sulfates, such as, sodium, ammonium and triethanolamine salts of $C_{12}$ to $C_{18}$ alkylsulfates, sodium $C_{12}$ to $C_{14}$ olefin sulfates, sodium laureth-6 carboxylate, sodium $C_{12}$ to $C_{18}$ pareth sulfate, and the like.

Cationic surfactants can have a hydrophobe that carries a positive charge or that is uncharged at pH values close to neutrality or lower, such as alkylamines, alkyl imidazolines, ethoxylated amines, and quaternary ammonium compounds. Cationic surfactants used in cosmetics are preferably N-derivatives and the neutralizing anion may be inorganic or organic. Among the cationic surfactant materials useful herein are quaternary ammonium compounds corresponding to the general formula: $(R^{14}R^{15}R^{16}R^{17}N^+)E^-$, wherein each of $R^{14}$, $R^{15}$, $R^{16}$, and $R^{17}$ are independently selected from an aliphatic group having from 1 to about 30 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g. chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated.

Alkylamines can be salts of primary, secondary and tertiary fatty $C_{12}$ to $C_{22}$ alkylamines, substituted or unsubstituted, and substances sometimes referred to as "amidoamines". Non-limiting examples of alkyl amines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane). Non-limiting examples of amidoamines and salts thereof include stearamido propyl dimethyl amine, stearamidopropyl dimethylamine citrate, palmitamidopropyl diethylamine, and cocamidopropyl dimethylamine lactate. Other cationic surfactants include distearyldimonium chloride, dicetyldimonium chloride, guar hydroxypropyltrimonium chloride, and the like. At low pH, amine oxides may protonate and behave similarly to N-alkyl amines.

Non-limiting examples of alkyl imidazolines include alkyl hydroxyethyl imidazoline, such as stearyl hydroxyethyl imidazoline, coco hydroxyethyl imidazoline, ethyl hydroxymethyl oleyl oxazoline, and the like. Non-limiting examples of ethyoxylated amines include PEG-cocopolyamine, PEG-15 tallow amine, quaternium-52, and the like.

Quaternary ammonium compounds are monomeric or polymeric materials containing at least one nitrogen atom that is linked covalently to four alkyl and/or aryl substituents, and the nitrogen atom remains positively charged regardless of the environmental pH. Quaternary ammonium compounds comprise a large number of substances that are used extensively as surfactants, conditioners, antistatic agents, and antimicrobial agents and include, alkylbenzyldimethyl ammonium salts, alkyl betaines, heterocyclic ammonium salts, and tetraalkylammonium salts. Long-chain (fatty) alkylbenzyldimethyl ammonium salts are preferred as conditioners, as antistatic agents, and as fabric softeners, discussed in more detail below. Other quaternary ammonium compounds include quaternary ammonium silicones. An extensive listing of quaternary ammonium compounds suitable for use herein and their functions appears in the INCI Dictionary, generally, and in Vol. 2, Section 4 of the Seventh Edition, both of which are incorporated herein by reference.

Non-limiting examples of alkylbenzyldimethylammonium salts include stearalkonium chloride, benzalkonium chloride, quaternium-63, olealkonium chloride, didecyldimonium chloride, and the like. Alkyl betaine compounds include alkylamidopropyl betaine, alkylamidopropyl hydroxysultaine, and sodium alkylamido propyl hydroxyphostaine. Non-limiting examples of alkyl betaine compounds include oleyl betaine, coco-betaine, cocamidopropylbetaine, coco-hydroxy sultaine, coco/oleamidopropyl betaine, coco-sultaine, cocoamidopropylhydroxy sultaine, and sodium lauramidopropyl hydroxyphostaine. Heterocyclic ammonium salts include alkylethyl morpholinium ethosulfate, isostearyl ethylimidonium ethosulfate, and alkylpyridinium chlorides, and are generally used as emulsifying agents. Non-limiting examples of heterocyclic ammonium salts include cetylpyridinium chloride, isostearylethylimidonium ethosulfate, and the like. Non-limiting examples of tetraalkylammonium salts include cocamidopropyl ethyldimonium ethosulfate, hydroxyethyl cetyldimonium chloride, quaternium-18, and cocodimonium hyroxypropyl hydrolyzed protein, such as hair keratin, and the like.

Suitable amphoteric or zwitterionic surfactants for use in the present compositions include those broadly described as derivatives of aliphatic quaternary ammonium, phosphonium, and sulfonium compounds, wherein which the aliphatic radicals can be straight chain or branched, and wherein one of the aliphatic substituents contains about 8 to about 30 carbon atoms and another substituent contains an anionic water-solubilizing group, such as carboxy, sulfonate, sulfate, phosphate, phosphonate, and the like. Classes of zwitterionics include alkylamino sulfonates, alkyl betaines and alkylamido betaines, such as stearamidopropyldimethylamine, diethylaminoethylstearamide, dimethylstearamine, dimethylIsoyamine, soyamine, myristylamine, tridecylamine, ethylstearylamine, N-tallowpropane diamine, ethoxylated (5 moles ethylene oxide) stearylamine, dihydroxy ethyl stearylamine, arachidylbehenylamine, and the like. Some suitable betaine surfactants include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, and acyl glutamates, wherein the alkyl and acyl groups have from 8 to 18 carbon atoms. Non-limiting examples of preferred amphoteric surfactants include cocamidopropyl betaine, sodium cocoamphoacetate, disodium cocoamphodiacetate, cocamidopropyl hydroxysultaine, and sodium cocoamphopropionate, which are particularly suitable as mild-type cleansers for skin and hair.

Nonionic surfactants are generally uncharged amphiphiles and usually are alkoxylated to varying degrees. Classes of nonionic surfactants include alcohols, alkanolamides, amine oxides, alkyl glucosides, esters, and ethers. Nonionic alcohols are usually hydroxy derivatives of long-chain $C_8$ to $C_{18}$ alkane hydrocarbons, such as cetearyl alcohol, hydrogenated tallow alcohol, lanolin alcohols, alkanolamides, and the like. Alkanolamides contain at least one alkoxyl or one polyoxyethylene grouping and include alkanol-derived amides, such as acylamide DEA, N-alkyl pyrrolidone, palmamide MEA, peanutamide MIPA, and the like and ethoxylated amides, such as PEG-50 tallow amide. Amine oxides include alkylamine oxides, such as lauramine oxide; and acylamidopropyl morpholine oxides, such as cocamidopropylamine oxide; and the like. The alkyl glucosides include linear and branched $C_4$ to $C_{24}$ alkyl glucosides, such as for example nonyl, decyl, dodecyl and lauryl glycoside. Esters include ethoxylated carboxylic acids, such as PEG-8 dilaurate, PEG-8 laurate, and the like; ethoxylated glycerides, such as PEG-4 castor oil, PEG-120 glyceryl stearate, triolein PEG-6 esters, and the like; glycol esters and derivatives thereof, such as glycol stearate SE, propylene glycol ricinoleate, and the like; monoglycerides, such as glyceryl myristate, glyceryl palmitate lactate, and the like; polyglyceryl esters, such as polyglyceryl-6-distearate, polyglyceryl-4 oleyl ether, and the like, polyhydric alcohol esters and ethers, such as methyl gluceth-20 sesquistearate, sucrose distearate; and the like; sorbitan/sorbitol esters, such as polysorbate-20, polysorbate-60, sorbitan sequiisostearate, and the like; and triesters of phosphoric acid, such as trideceth-3 phosphate, trioleth-8 phosphate, and the like. Exemplary ethers include ethoxylated alcohols, such as, Ceteareth-10, Ceteth-10, Ceteth-20, Isoceteth-20, Steareth-10, Steareth-16, Steareth-20, Steareth-25, Oleth-2, Oleth-10, Oleth-20, nonoxynol-9, and the like; ethoxylated lanolin, such as PEG-20 lanolin, PPG-12-PEG-65 lanolin oil, and the like; ethoxylated polysiloxanes, such as dimethicone copolyol, and the like; propoxylated POE ethers, such as meroxapol 314, poloxamer 122, PPG-5-ceteth-20, and the like; and alkyl polyglycosides, such as lauryl glucose, and the like.

Non-limiting examples of nonionic surfactants include linear or branched alcohol ethoxylates, $C_8$ to $C_{12}$ alkylphenol alkoxylates, such as octylphenol ethoxylates, polyoxyethylene polyoxypropylene block copolymers, and the like; $C_8$ to $C_{22}$ fatty acid esters of polyoxyethylene glycol mono- and di-glycerides; sorbitan esters and ethoxylated sorbitan esters; $C_8$ to $C_{22}$ fatty acid glycol esters; block copolymers of ethylene oxide and propylene oxide; and the like. Non-limiting examples of surfactant boosters or hydrotropes include alkanolamides, such as acetamide MEA, monoethanolamide, diethanolamide, lauramide DEA, cocamide MEA, cocamide DEA, isopropanolamide, and the like; amine oxides, such as hydrogenated tallowamine oxide; short chain alkyl aryl sulfonates, such as sodium toluene sulfonate; sulfosuccinates, such as disodium stearyl sulfosuccinate; and the like.

Any known conditioning agent is useful in the hair fixative compositions of this invention. Conditioning agents function to improve the sensory and physical attributes of the hair and scalp, e.g., improvement in softness, feel, and body (fullness), promotion of detangling under wet and dry combing conditions, reduction or elimination of static charge from the hair and/or skin, etc. In one aspect of the invention, the conditioning agents can be selected from synthetic oils, natural oils (e.g., vegetable, plant and animal oils), mineral oils, natural and synthetic waxes, cationic polymers, cationic surfactants, monomeric and polymeric quaternized ammonium salt compounds, silicones (e.g., silicone oils, resins and gums), proteins, hydrolyzed proteins, fatty acids, fatty amines; and mixtures thereof.

The synthetic oils include polyolefins, e.g., poly-α-olefins such as polybutenes, polyisobutenes and polydecenes. The polyolefins can be hydrogenated. Fluorinated or perfluorinated oils are also contemplated within the scope of the present invention. Fluorinated oils include perfluoropolyethers described in EP-A-486135 and the fluorohydrocarbon compounds described in WO 93/11103. The fluorinated oils may also be fluorocarbons such as fluoramines, e.g., perfluorotributylamine, fluoridated hydrocarbons, such as perfluorodecahydronaphthalene, fluoroesters, and fluoroethers.

Suitable natural oils include but are not limited to peanut, sesame, avocado, coconut, cocoa butter, almond, safflower, corn, cotton seed, sesame seed, walnut oil, castor, olive, jojoba, palm, palm kernel, soybean, wheat germ, linseed, sunflower seed; eucalyptus, lavender, vetiver, litsea, cubeba, lemon, sandalwood, rosemary, chamomile, savory, nutmeg, cinnamon, hyssop, caraway, orange, geranium, cade, and bergamot oils, fish oils, glycerol tricaprocaprylate; and mixtures thereof.

Suitable natural and synthetic waxes include but are not limited to carnauba wax, candelila wax, alfa wax, paraffin wax, ozokerite wax, olive wax, rice wax, hydrogenated jojoba wax, bees wax, modified bees wax, e.g., cerabellina wax, marine waxes, polyolefin waxes, e.g., polyethylene wax; and mixtures thereof.

In one aspect, suitable cationic polymers include but are not limited to homopolymers and copolymers derived from free radically polymerizable acrylic or methacrylic ester or amide monomers. The copolymers can contain one or more units derived from acrylamides, methacrylamides, diacetone acrylamides, acrylic or methacrylic acids or their esters, vinyllactams such as vinyl pyrrolidone or vinyl caprolactam, and vinyl esters. Exemplary polymers include copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT™ by International Specialty Products; the dimethyl amino ethyl methacrylate/vinyl caprolactam/vinyl pyrrolidone terpolymers, such as the product sold under the name GAFFIX™ VC 713 by International Specialty Products; the vinyl pyrrolidone/methacrylamidopropyl dimethylamine copolymer, marketed under the name STYLEZE™ CC 10 by International Specialty Products; and the vinyl pyrrolidone/quaternized dimethyl amino propyl methacrylamide copolymers such as the product sold under the name GAFQUAT™ HS 100 by International Specialty Products.

In a still further aspect suitable cationic polymer conditioners are selected from the quaternary polymers of vinyl pyrrolidone and vinyl imidazole such as the products sold under the trade name Luviquat® (product designation FC 905, FC 550, and FC 370) by BASF.

Other non-limiting examples of quaternary ammonium compounds useful as cationic conditioners in the present invention include acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, quaternium-26, quaternium-27, quaternium-53, quaternium-63, quaternium-70, quaternium-72, quaternium-76 hydrolyzed collagen, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, polymers and copolymers of dimethyl diallyl ammonium chloride, such as Polyquaternium-4, Polyquaternium-6, Polyquaternium-7, Polyquaternium-10, Polyquatemium-11, Polyquarternium-16, Polyquaternium-22, Polyquaternium-24, Polyquaternium-28, Polyquaternium-29, Polyquaternium-32, Polyquaternium-33, Polyquaternium-35, Polyquaternium-37, Polyquaternium-39, Polyquaternium-44, Polyquaternium-46, Polyquaternium-47, Polyquaternium-52, Polyquaternium-53, Polyquarternium-55, Polyquaternium-59, Polyquaternium-61, Polyquaternium-64, Polyquaternium-65, Polyquaternium-67, Polyquaternium-69, Polyquaternium-70, Polyquaternium-71, Polyquaternium-72, Polyquaternium-73, Polyquaternium-74, Polyquaternium-76, Polyquaternium-77, Polyquaternium-78, Polyquaternium-79, Polyquaternium-80, Polyquaternium-81, Polyquaternium-82, Polyquaternium-84, Polyquaternium-85, Polyquaternium-87, PEG-2-cocomonium chloride, and mixtures thereof.

Other cationic polymer conditioners that can be used in the fixative compositions of the invention include polyalkyleneimines such as polyethyleneimines, polymers containing vinyl pyridine or vinyl pyridinium units, condensates of polyamines and epichlorhydrins, quaternary polyurethanes, and quaternary derivatives of chitin.

Exemplary cationic surfactants include the cationic surfactants disclosed hereinabove as well as salts of a primary, secondary, or tertiary fatty amine, optionally polyoxyalkylenated; a quaternary ammonium salt derivative of imadazoline, or an amine oxide. Suitable examples include mono-, di-, or tri-alkyl quaternary ammonium compounds with a counterion such as a chloride, methosulfate, tosylate, including, but not limited to, cetrimonium chloride, dicetyldimonium chloride, behentrimonium methosulfate, and the like.

The conditioning agent can be any silicone known by those skilled in the art to be useful as a conditioning agent. The silicones may be present in the form of fluids, oils, waxes, resins, gums, and mixtures thereof. They can be volatile or non-volatile and soluble or insoluble in the fixative composition. The silicones can be selected from polyalkyl siloxanes, polyaryl siloxanes, polyalkyl aryl siloxanes, polyorgano siloxanes modified by organofunctional groups, and mixtures thereof. The silicones suitable for use according to the invention include the silicone containing polymers and copolymers described in the emulsifier and emollient disclosure hereinabove.

Suitable polyalkyl siloxanes include polydimethyl siloxanes with terminal trimethyl silyl groups or terminal dimethyl silanol groups (dimethiconol) and polyalkyl ($C_1$-$C_{20}$) siloxanes.

Suitable polyalkyl aryl siloxanes include polydimethyl methyl phenyl siloxanes and polydimethyl diphenyl siloxanes, linear or branched.

The silicone gums suitable for use herein include polydiorganosiloxanes. In one aspect the silicone gums have a number-average molecular weight between 200,000 and 1,000,000 Daltons. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane.

Suitable silicone resins include silicones with a dimethyl/trimethyl siloxane structure and resins of the trimethyl siloxysilicate type.

The organo-modified silicones suitable for use in the invention include silicones containing one or more organo-functional groups attached by means of a hydrocarbon radical and grafted siliconated polymers. Exemplary organo-modified silicones are amino functional silicones.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having quaternary ammonium moieties on the polypeptide chain, including at least one $C_1$-$C_{18}$ alkyl moiety. Hydrolyzed proteins include Croquat™ L, in which the quaternary ammonium groups include a $C_{12}$ alkyl group, Croquat™ M, in which the quaternary ammonium groups include $C_{10}$-$C_{18}$ alkyl groups, Croquat™ S in which the quaternary ammonium groups include a $C_{18}$ alkyl group and Crotein™ Q in which the quaternary ammonium groups include at least one $C_1$-$C_{18}$alkyl group. These products are sold by Croda International. Quaternized vegetable proteins such as wheat, corn, or soy proteins such as cocodimonium, hydrolyzed wheat protein, laurdimonium hydrolyzed wheat protein and steardimonium hydrolyzed wheat protein are also useful as conditioning agents.

Suitable fatty acids that can be used as conditioning agents are those previously described as emulsifiers, including $C_{12}$-$C_{22}$ fatty acids. Exemplary fatty acid conditioners include but are not limited to myristic acid, palmitic acid, stearic acid, oleic acid, linoleic acid, isostearic acid, and behenic acid.

Suitable fatty amines known to be useful as a conditioning agent; e.g. dodecyl, cetyl or stearyl amines, such as stearamidopropyl dimethylamine are also useful in the fixative compositions of the invention.

The conditioning agent(s) can be present in an amount of 0.001 wt. % to 20 wt. % in one aspect, from 0.01 wt. % to 10 wt. % in another aspect, and from 0.1 wt. % to 3 wt. % based on the total weight of the fixative composition.

In addition to the one or more cosmetically acceptable adjuvants and additives described hereinabove, the fixative composition of the present invention can contain one or more additional cosmetically acceptable adjuvants and/or additives chosen from protecting and therapeutic agents, such as UV filters, antiradical agents, antioxidants, hair-loss agents, vitamins and pro-vitamins, proteinaceous materials and derivatives thereof; hair colorants, such as pigments and dyes for the temporary, semi-permanent, or permanent coloring of the hair; hair bleaching agents; hair highlighting agents; polymer film modifying agents, such as plasticizers, humectants, tackifiers, detackifiers, wetting agents, and the like; product finishing agents, such as chelating agents, sequestrants, buffers, opacifiers, pearlizing agents, and stabilizers; aliphatic monoalcohols, such as methyl alcohol, ethyl alcohol, n-propyl alcohol, isopropyl alcohol, n-butyl alcohol, isobutyl alcohol, t-butyl alcohol, and amyl alcohol (all isomers); polyols such as glycols and glycerol; botanical extracts; oxidizing agents; reducing agents; lubricants; electrolytes; hair sheen enhancers; preservatives; fragrances; solubilizers; chemical hair waving or straightening agents; and detangling/wet combing agents. These adjuvants and additives can be present in the composition in amounts that range from 0 to 20 wt. % in relation to the total weight of the fixative composition. The precise amount of each adjuvant and additive to employ in a desired composition can be easily determined by one of ordinary skill in the field according to the nature and function of the ingredient. Those skilled in the hair setting art recognize that some ingredients described herein are multifunctional and, hence, can serve more than one purpose in the formulation, as long as the purpose and properties of the hair setting composition performs its intended function. An extensive listing of cosmetic ingredients and.their functions appears in the INCI Dictionary, generally, and in Vol. 2, Section 4 of the Seventh Edition, both of which are incorporated herein by reference.

While overlapping weight ranges for the various ingredients, adjuvants and additives contained in the fixative compositions, of the invention have been disclosed for selected embodiments and aspects of the invention, it should be readily apparent that the specific amount of each component in the fixative composition is selected from its disclosed range such that the amount of each component is adjusted so that the sum of all components in the composition will total 100 weight percent. The amounts of each component employed in the fixative composition will vary with the compatibility, purpose, and character of the desired component and can be readily determined by one skilled in the formulation arts and from the literature.

The following examples further describe and demonstrate embodiments within the scope of the present invention. These examples are presented solely for the purpose of illustration, and are not to be construed as limitations of the present invention since many variations thereof are possible without departing from the spirit and scope thereof. Unless otherwise specified, weight percents (wt. %) are given in wt. % based on the weight of the total composition.

Methods Description

High Humidity Curl Retention (HHCR) Test

The resistance of a polymer fixative composition to high humidity (about 90% Relative Humidity (RH)) is measured by its ability to hold a curl set on hair after absorption of water from the applied composition and from the surrounding atmosphere employing the well known technique commonly referred to as high humidity curl retention (HHCR). Descriptions of the HHCR methodology are readily found in the cosmetic literature (see, for example, Ch. 30, Harry's Cosmeticology, 8th Ed., M. J. Rieger, Ph.D. (ed.), pp. 666-667, Chemical Publishing Co., Inc., New York, N.Y., 2000, and Diaz et al., J. Soc. Cosmet. Chem., 34, pp. 205-212, July 1983, the relevant disclosures of each are incorporated herein by reference.

Tresses of commercially blended untreated (virgin) human hair are prepared employing natural brown or black color European and/or Oriental hair supplied by International Hair Importers and Products Inc., New York. Each hair tress (about 2.5 grams weight) is about 7.5 inches in length and is crimped (by the root portion) within a metal clamp equipped with a wire hanger loop. Prior to use, each tress is washed with a dilute aqueous solution of sodium lauryl sulfate (10% SLS) followed by thorough rinsing with deionized water at ambient room temperature. The tresses are dried by towel blotting. The initial extended length of the hair tress ($L_e$) is measured and recorded. Varying amounts of polymer fixative composition to be evaluated are applied to each hair tress. The polymer fixative composition to be evaluated is applied to the hair tress and distributed uniformly from the root portion of the hair to tip portion. The treated hair tress is wrapped around a hair curler having an outer diameter of about 3 cm and dried for 12 hours at ambient room temperature of about 21 to 23° C. After drying, the curler is carefully removed, leaving the hair tress styled into a single curl, the initial length of the hair curl ($L_i$) is measured and recorded. The curled hair tress is vertically hung in a humidity chamber set at a temperature of about 26° C. and a relative humidity level of 90%.

High humidity curl retention is determined by measuring the length of the hair curl as the curl relaxes. Measurements are taken at selected intervals of time ($L_t$) over a 24 hour continuum of exposure to high humidity. The following equation is used to calculate percent curl retention, relative to the initial curl length ($L_i$) and length of the fully extended hair, before curling ($L_e$):

$$\% \text{ Curl Retention} = L_e - L_t / L_e - L_i \times 100$$

The change in curl length (droop, helix formation) is periodically measured at selected intervals and is monitored over a period of 24 hours. An initial measurement is taken at time zero, followed by measurements at 0.25 hour intervals for the first hour of exposure, followed by measurements taken at 0.5 hour intervals for the second hour of exposure, followed by measurements taken at 1.0 hour intervals for the remaining 22 hours of exposure.

A curl retention of about 70% or more for a minimum period of about 0.75 hours at about 90% RH is a conventional benchmark for good high humidity resistance, and an HHCR greater than 70% after a period of at least about 3 hours is deemed very good to excellent.

High Humidity Spiral Curl Retention Test (HHSCR)

While the humidity resistance of a fixative composition can be evaluated by the HHCR test described above. The HHCR test is performed using regular salon roller type curlers, where the hair overlaps onto itself as it is rolled, which protects the fibers inside the curl from the test environment. The curl retention test can be rendered more stringent by using of spiral curlers. With this modification, hair is rolled into a spiral groove down the length of the curler rod without overlap. Thus, for a spiral curl, the entire length of the hair is fully exposed to the environment.

The same materials, methods, and evaluation techniques outlined for the previously described HHCR test are employed for the HHSCR test except that the hair tress weighs 0.5 g, is 6.5 inches long and is wrapped around a spiral perm rod (Cyber Sprials™ large spiral curling rods, 8 mm inner diameter, 13.5 mm outer diameter, 162 mm length, American Discount Beauty Supply, 269 South Beverly Drive #250, Beverly Hills, Calif.). The results are reported as percent curl retention calculated by the curl retention equation set forth above.

A curl retention of about 70% or more for a minimum period of about 0.75 hours at about 90% RH is a conventional benchmark for good high humidity resistance, and an HHCR greater than 70% after a period of at least about 3 hours is deemed very good to excellent.

Mechanical Stiffness Test Method

A TA XTPlus Texture Analyser (Stable Micro Systems, Surrey, UK) fitted with a rectangular loading nose (3 mm thick×70 mm wide×99 mm high) and a 3-point bending rig is employed to evaluate the mechanical stiffness of a fixative treated hair tress. The Texture Analyser is interfaced with a personal computer loaded with Texture Exponent 32 data acquisition software that collects and analysis the data inputted from the instrument. The bending rig consists of two parallel support legs that are spaced apart by approximately 25.4 mm. The treated hair swatch test sample is centered across the span of the support legs and the loading nose which is centered above and between the support legs is pressed through the sample at a rate of 40 mm/s for a distance of 20 mm. Data acquisition starts when the loading nose contacts the sample. The data acquisition software calculates and records the amount of force (Newtons) it takes to deflect the sample through a distance of 20 mm. The results are reported as Peak Force (N) and Work (N·mm).

Hair swatches (6.5" long, 2.5 g in weight) consisting of virgin natural human hair are bound with a flat (sewn and waxed) binding so that the tress has a uniform rectangular cross section along its whole length. The tresses are washed with a stripping shampoo containing 10 wt. % ammonium lauryl sulfate and rinsed with deionized water. A designated amount of experimental fixative is evenly applied to the damp hair swatches. A first set of swatches are laid flat on Teflon® foil to dry at 23° C. and 50% relative humidity in a controlled laboratory environment for 16 hours and tested. A second set of swatches is similarly prepped and subsequently placed in a humidity chamber (Espec LHU-113) set at 23° C. and 90% relative humidity for 16 hours and subsequently tested for mechanical stiffness.

Molecular Weight Determination

The molecular weight of the cationic Cassia galactomannan polymer is determined by a low angle light scattering detector (Triple Detector Array, model no. 302-040) coupled with two Visco GEL C-MBHMW-3078 columns using a sample concentration of 0.6 mg/ml in a 0.05 M ammonium acetate/10% methanol solvent (at a pH of 4.0), an injection volume of 100 µL, a column temperature of 30° C., and a flow rate of 0.9 mL/min.

Viscosity

Brookfield rotating spindle method: The viscosity of each polymer containing composition is measured as mPa·s, employing a Brookfield rotating spindle viscometer, Model RVT (Brookfield Engineering Laboratories, Inc.), at about 20 revolutions per minute (rpm), at ambient room temperature of about 20 to 25° C. (hereafter referred to as viscosity). Appropriate spindle sizes are set forth in the examples.

Yield Value

Yield Value, also referred to as Yield Stress, is defined as the initial resistance to flow under stress. It is measured by the Brookfield Yield Value (BYV) Extrapolation Method using a Brookfield viscometer (Model RVT). The Brookfield viscometer is used to measure the torque necessary to rotate a spindle through a liquid sample at speeds of 0.5 to 100 rpm. Multiplying the torque reading by the appropriate constant for the spindle and speed gives the apparent viscosity. Yield Value is an extrapolation of measured values to a shear rate of zero. The BYV is calculated by the following equation:

$$BYV, dyn/cm^2 = (\eta_{\alpha 1} - \eta_{\alpha 2})/100$$

where $\eta_{\alpha 1}$ and $\eta_{\alpha 2}$=apparent viscosities obtained at two different spindle speeds (0.5 rpm and 1.0 rpm, respectively). These techniques and the usefulness of the Yield Value measurement are explained in Technical Data Sheet Number 244 (Revision: 5/98) from Noveon Consumer Specialties of Lubrizol Advanced Materials, Inc., herein incorporated by reference. Low yield values (<50 dyns/cm$^2$) are indicative of smooth and Newtonian-like flow properties.

EXAMPLE 1

This example describes the preparation of cationic Cassia (Cassia hydroxypropyltrimethyl ammonium chloride). To a reaction vessel 160 g of Cassia gum (containing about 10% moisture) is mixed in a solution of 921 g of 44% isopropanol in water. To this mixture 4.5 g of potassium hydroxide is added and the mixture is heated at 40° C. for 30 minutes under nitrogen until a slurry is formed. Subsequently, 92.8 g of 2,3-epoxypropyltrimethyl ammonium chloride (Quab 151 from SKW Quab Chemicals Inc, 70%) is added to the slurry. The reaction slurry is heated to 70° C. and is kept at this temperature for 3 hours. After cooling to 50° C., the slurry is diluted with 380 g of 99% isopropanol and neutralized to a pH of about 7.0 with a solution of acetic acid (50 wt. % solution in deionized water). The Cassia hydroxypropyltrimethyl ammonium chloride product is filtered, washed once with 380 g of isopropanol (99 wt. %), air dried overnight and oven dried at 100° C. for 4 hours to produce 179.3 of cationic Cassia. The final product has a nitrogen content of 2.18 wt. % calculated on a dry weight basis of the polymer (dry wt. basis) and a charge density of 1.56 meq/g. The charge density of cationically functionalized Cassia can be changed by varying the stoichiometric amount of cationic functionalization agent employed in the functionalization reaction. The quaternary nitrogen content (and thus the cationic charge density) of cationic Cassia is increased or decreased by increasing or decreasing the stoichiometric amount of quaternizing agent relative to the hydroxyl content present on the Cassia backbone.

EXAMPLE 2

Aqueous dispersions in deionized water containing 2 wt. % of the cationic Cassia and cationic guar samples set forth in Table 1 below are evaluated for mechanical stiffness properties as described in the Mechanical Stiffness Test Method above. Asian (Chinese) type hair swatches are prepared and treated (0.8 g of fixative composition/swatch) and evaluated for mechanical stiffness after exposure to 50% and 90% relative humidity conditions. Five replicates of each test sample are prepared and tested. The average peak force for the 5 replicates are calculated and recorded in Table 1.

TABLE 1

| Sample | Cationic Charge Density (meq/g). | Relative Humidity (%). | Work (N · mm) | Peak Force (N) |
|---|---|---|---|---|
| Cationic Cassia | 1.8 | 50 | 80.4 | 12.2 |
| Cationic Cassia | 3 | 50 | 48.8 | 7.6 |
| Cationic Guar* | 1.76 | 50 | 38.2 | 7.0 |
| Cationic Guar* | 2.9 | 50 | 31.8 | 5.4 |
| Cationic Cassia | 1.8 | 90 | 37.6 | 5.9 |

TABLE 1-continued

| Sample | Cationic Charge Density (meq/g). | Relative Humidity (%). | Work (N · mm) | Peak Force (N) |
|---|---|---|---|---|
| Cationic *Cassia* | 3 | 90 | 60.7 | 9.0 |
| Cationic Guar* | 1.76 | 90 | 28.8 | 4.2 |
| Cationic Guar* | 2.9 | 90 | 31.1 | 4.7 |

*Prepared in a manner similar to Example 1

At equivalent charge densities, cationic *Cassia* polymers demonstrate higher stiffness (higher peak force and Work) than cationic guar, both at 50% and 90% relative humidity environment on Chinese hair swatches.

EXAMPLE 3

Two separate fixative gel compositions (A and B) containing 2 wt. % of the cationic *Cassia* polymers of the invention are formulated in combination with 1 wt. % (total polymer actives) of an acid swellable associative rheology modifier (Carbopol® Aqua CC, Lubrizol Advanced Materials, Inc.; INCI Name: Polyacrylates-1 Crosspolymer). The cationic *Cassia* polymers are prepared by the method set forth in Example 1 except that the cationic *Cassia* contained in composition (A) contains 4.2 wt. % nitrogen (dry wt. basis) and a charge density of 3.0 meq/g, and the cationic *Cassia* contained in composition (B) contains 2.3 wt. % nitrogen (dry wt. basis) and a charge density of 1.6 meq/g. An identically formulated gel fixative composition utilizing a commercially available cationic guar, Jaguar™ Cl 3S (Rhodia, Inc.), containing 1.5 wt. % nitrogen (dry wt. basis) and a charge density of 1.0 meq/g is prepared for comparative HHSCR test evaluations.

The tresses for this test are comprised of European brown hair, weighing 0.5g, 6.5 inches long and 0.5 inches wide. To each tress 0.1g of the polymer gel is uniformly applied and the treated tresses are tested as set forth in the HHSCR Test methodology disclosed above. Ten replicates of each of the fixative treated tresses were evaluated and the average percent retention values are plotted in FIG. 1.

The cationic *Cassia* fixative gels (in combination with Polyacrylates-1 Crosspolymer) display superior spiral curl retention properties at high humidity compared to the commercially available cationic guar, Jaguar™ C13S, independent of cationic *Cassia* charge density. Both cationic *Cassia* polymers (Composition (A) charge density: 3.0 meq/g and Composition (B) charge density: 1.6 meq/g) display over 85% spiral curl retention after 24 hours at 90% relative humidity and 23° C. In comparison, cationic guar, Jaguar™ C13S (charge density: 1 meq/g) displays 60% spiral curl retention after 24 hours at 90% relative humidity and 23° C.

EXAMPLE 4

The fixative gel compositions of Example 3 are evaluated for mechanical stiffness properties as described in the Mechanical Stiffness Test Method above. European brown hair swatches are prepared and treated (0.8 g of fixative composition/swatch) and evaluated for mechanical stiffness after exposure to 47% and 90% relative humidity conditions. Five replicates of each test sample are prepared and tested. The average peak force for the 5 replicates are calculated and recorded in Table 2.

TABLE 2

| Sample | Relative Humidity (%) | Work (N · mm) | Peak Force (N) |
|---|---|---|---|
| 2 wt % Composition A (3 meq/g) | 47 | 61.8 | 9.9 |
| 2 wt % Composition B (1.6 meq/g) | 47 | 52.9 | 9.4 |
| 2 wt % Jaguar ™ C13S (1 meq/g) | 47 | 41.5 | 6.8 |
| 2 wt % Composition A (3 meq/g) | 90 | 46.0 | 6.5 |
| 2 wt % Composition B (1.6 meq/g) | 90 | 50.4 | 6.6 |
| 2 wt % Jaguar ™ C13S (1.0 meq/g) | 90 | 38.2 | 5.5 |

Both cationic *Cassia* fixative gel compositions display significantly higher stiffness (Peak Force and Work) than cationic guar at 47% relative humidity. The same trend but with less dramatic differences is observed at 90% relative humidity.

EXAMPLE 5

Figure 2:
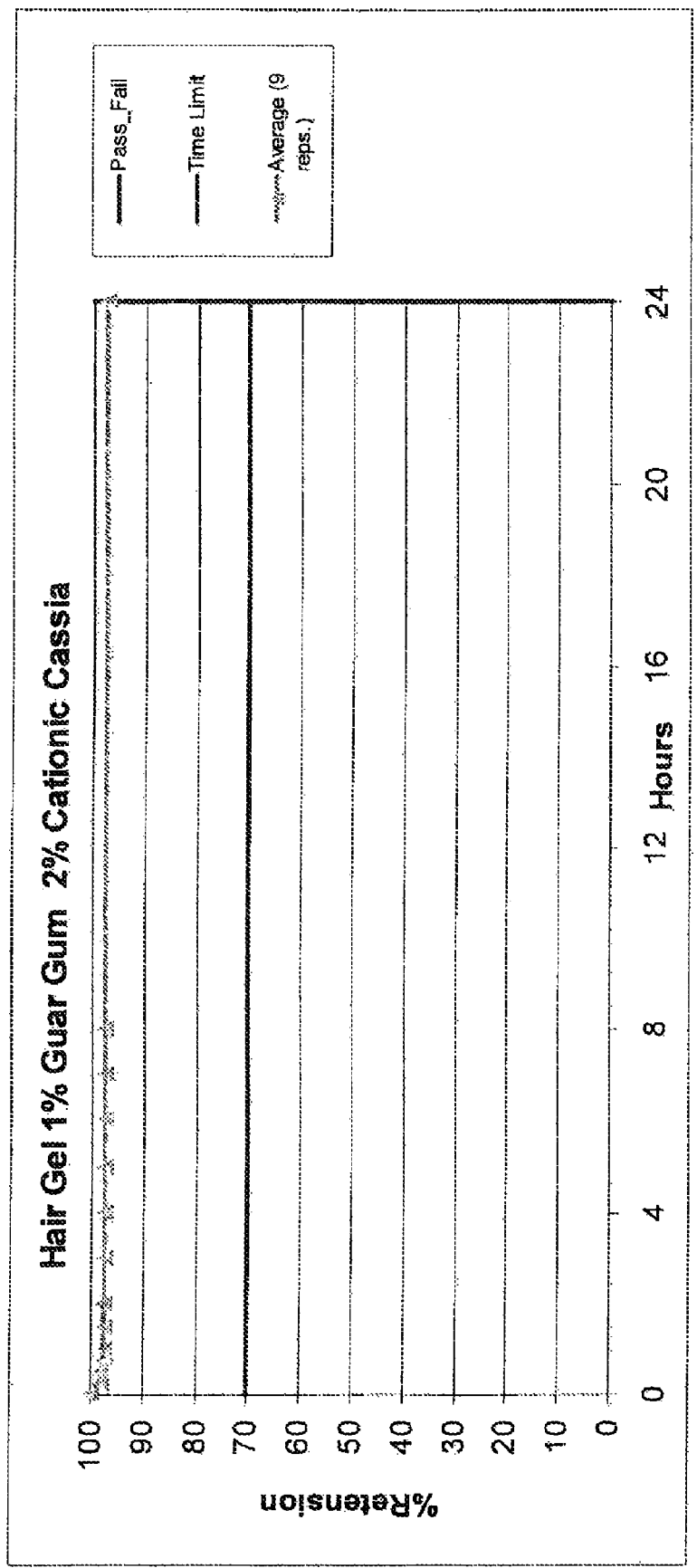
FIG. 2 is a plot of the percent high humidity curl retention vs. time obtained from fixative gel samples containing a blend of 2 wt. % cationic Cassia of the invention and 1 wt. % guar gum.

A fixative gel formulated with 2 wt. % of the cationic *Cassia* set forth in composition A of Example 3 (charge density: 3.0 meq/g) and 1 wt. % guar gum (Novegum G888, Lubrizol Advanced Materials, Inc.) is evaluated for curl retention as described in the HHCR Test. European brown hair swatches and hair tresses are utilized in the respective evaluations. Nine replicates of each treated hair swatch and hair tress are evaluated. The cationic *Cassia* polymer in combination with guar gum display excellent high humidity curl retention over 95.5% curl retention after 24 hours at 90% relative humidity and 23° C. The averages of the results are plotted in FIG. 2.

EXAMPLE 6

Aqueous fixative gels are made utilizing the cationic *Cassia* described in composition A of Example 3 (charge density: 3.0 meq/g) and guar gum (Novegum™ G888). The amounts of formulation components, viscosity and yield value data of the various gels are reported in Table 3.

TABLE 3

| Fixative Sample | Brookfield Viscosity at 20 rpm (mPa · s) | Spindle Size | Yield Value (dyn/cm$^2$) |
|---|---|---|---|
| 1 wt % Cationic *Cassia* (3 meq/g) in deionized water | 324 | 1 | 0 |
| 2 wt % Cationic *Cassia* (3 meq/g) in deionized water | 3,180 | 3 | 0 |
| 1 wt % guar (Novegum ™ G888) in deionized water | 4,310 | 3 | 22 |
| 2 wt % guar (Novegum ™ G888) in deionized water | 31,100 | 7 | 620 |
| Blend of 1 wt % cationic *Cassia* (3 meq/g) and 1 wt % guar gum (Novegum ™ G888) in deionized water | 17,300 | 4 | 160 |
| Blend of 2 wt % cationic *Cassia* (3 meq/g) and 1 wt % guar gum (Novegum ™ G888) in deionized water | 38,700 | 7 | 560 |

An unexpected synergy occurs (viscosity and yield value increase) when blends of the cationic *Cassia* of the invention and guar are formulated together.

EXAMPLE 7

The fixative compositions set forth in Example 6 are evaluated for mechanical stiffness properties as described in the Mechanical Stiffness Test Method above. European brown hair swatches are prepared and treated (0.8 g of fixative composition/swatch) and evaluated for mechanical stiffness after exposure to 90% relative humidity conditions. Five replicates of each test sample are prepared and tested. The average Peak Force and Work for the 5 replicates are calculated and recorded in Table 4.

TABLE 4

| Fixative Sample | Peak force (N) | Work (N · mm) |
| --- | --- | --- |
| 1 wt. % cationic Cassia (3 meq/g) in deionized water | 9.2 | 46.1 |
| 2 wt. % cat Cassia in deionized water | 13.7 | 68.2 |
| 1 wt. % guar gum (Novegum ™ G888) in deionized water | 4.9 | 33.9 |
| 2 wt. % guar gum (Novegum ™ G888) in deionized water | 4.9 | 33.9 |
| Blend 1 wt. % cationic Cassia (3 meq/g) and 1 wt % guar gum (Novegum ™ G888) in deionized water | 14.9 | 81.2 |
| Blend 2 wt. % cationic Cassia (3 meq/g) and 1 wt % guar gum (Novegum ™ G888) in deionized water | 15.3 | 90.5 |

Figure 3:
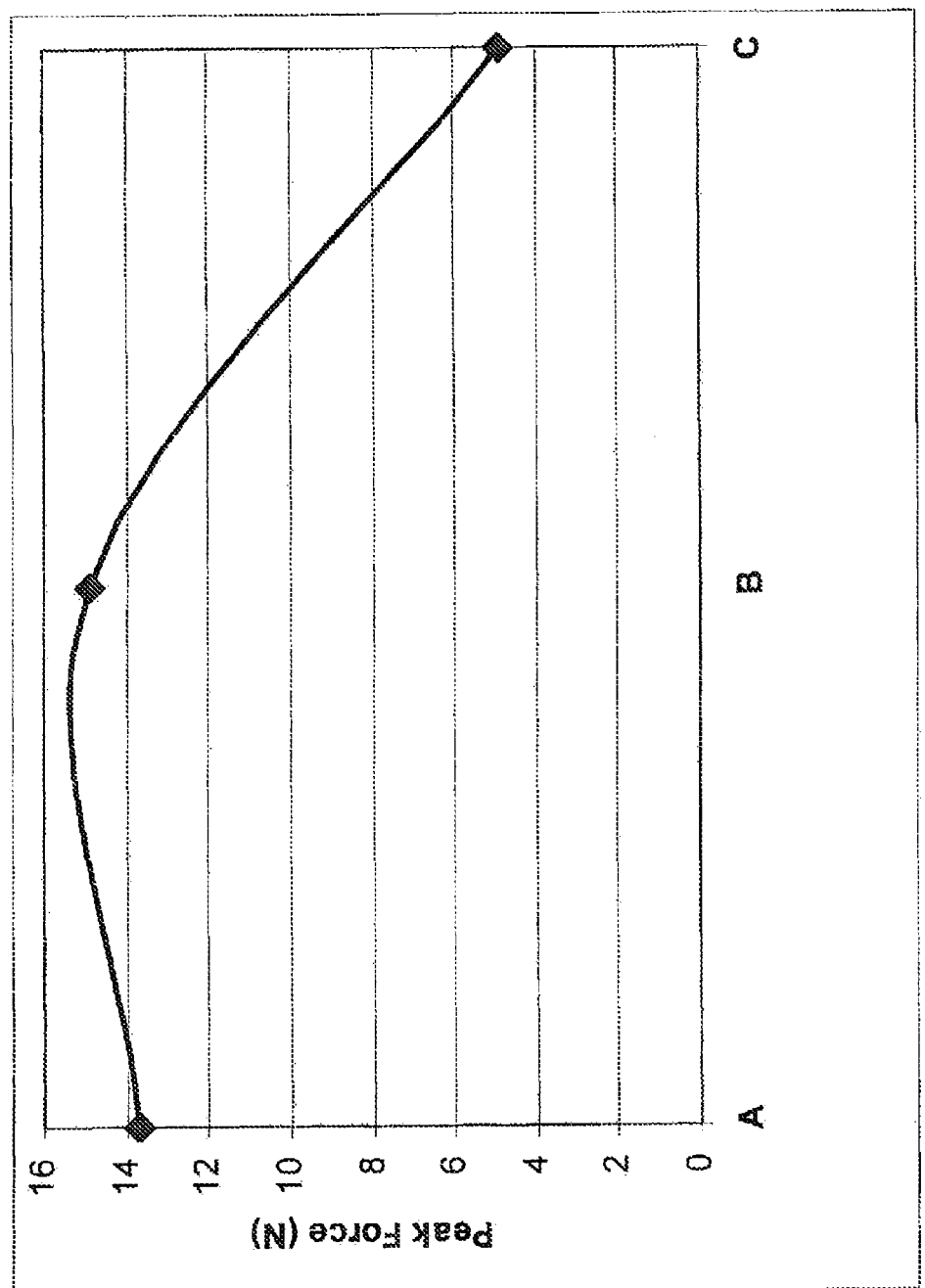
FIG. 3 is a plot of the Peak Force (Newtons) needed to deflect fixative treated hair swatches centered across the span of two support legs of a 3-point bending rig.

The cationic Cassia polymer fixative compositions display high stiffness values. The gels made of a blend of cationic Cassia (charge density: 3 meq/g) and guar gum Novegum™ G888 display even higher synergistic stiffness (higher peak force and work) at 90% relative humidity at 23° C. compared to the individual neat components. The peak force values of the compositions are plotted in FIG. 3. In FIG. 3, Point A represents the 2 wt. % cationic Cassia (0 wt. % guar gum) in deionized water formulation, Point B represents the blend of 1 wt. % cationic Cassia and 1 wt % guar gum in deionized water formulation, and Point C represents the 2 wt. % guar gum (0 wt. % cationic Cassia) in deionized water formulation.

EXAMPLE 8

The fixative compositions set forth in Example 6 are evaluated on European brown hair tresses for curl retention in the HHSCR Test at 90% relative humidity at 23° C. To each tress 0.1 g of the fixative gel is uniformly applied and the treated tresses are tested as set forth in the HHSCR Test methodology disclosed above. Ten replicates of each of the fixative treated tresses were evaluated and the average percent curl retention values set forth in Table 5.

TABLE 5

| Fixative Sample | Spiral curl retention at 8 hours (%) | Spiral curl retention at 24 hours (%) |
| --- | --- | --- |
| 1 wt % cationic Cassia (3 meq/g) in deionized water | 85.3 | 85.9 |
| 2 wt % cationic Cassia in deionized water | 88.3 | 87.2 |
| 1 wt % Guar G888 in deionized water | 68.0 | 68.0 |
| 2 wt % guar g888 in deionized water | 79.8 | 77.6 |
| Blend 1 wt % cationic Cassia (3 meq/g) and 1 wt % guar gum (Novegum ™ G888) in deionized water | 89.7 | 89.7 |

TABLE 5-continued

| Fixative Sample | Spiral curl retention at 8 hours (%) | Spiral curl retention at 24 hours (%) |
| --- | --- | --- |
| Blend 2 wt % cationic Cassia (3 meq/g) and 1 wt % guar gum (Novegum ™ G888) in deionized water | 93.3 | 93.3 |

Both cationic Cassia dispersions (at 1 and 2 wt. %) and the gels made from a blend of cationic Cassia (3 meq/g) and guar gum (Novegum™ G888) display high excellent spiral curl retention after 8 and 24 hours at exposure to 90% relative humidity at 23° C.

What is claimed is:

1. A method of using a polygalactomannan as a hair fixative in a personal care composition comprising: applying said composition to the hair wherein said polygalactomannan contains a D-mannosyl to D-galactosyl residue ratio of at least 5 to 1, said D-mannosyl and D-galactosyl residues having pendant hydroxyl groups, and wherein a portion of the hydrogen groups on the pendant hydroxy substituents on the mannosyl and galactosyl residues are substituted with a group represented by the formula:

-AR$^1$ wherein A is a substituted or unsubstituted alkylene group containing 1 to 6 carbon atoms, and
R$^1$ is a group independently —N(R$^3$)$_3$$^+$X$^-$, —S(R$^3$)$_2$$^+$X$^-$, and
—P(R$^3$)$_3$$^+$X$^-$; wherein R$^3$ independently represents substituted and unsubstituted $C_1$ to $C_{24}$ alkyl, substituted and unsubstituted benzyl and substituted and unsubstituted phenyl; and X is any suitable anion that balances the charge on the onium cation.

2. A method as set forth in claim 1 wherein A is a alkylene radical substituted with one or more substituents selected from $C_1$ to $C_3$ alkyl, $C_1$ to $C_3$ haloalkyl, hydroxyl, and halogen.

3. A method as set forth in claim 1 wherein X is a halide.

4. A method as set forth in claim 1 wherein said polygalactomannan has a number average molecular weight ranging from 200,000 to 300,000 Daltons.

5. A method as set forth in claim 1 wherein at least one of said hydroxyl hydrogens is substituted by a substituent represented by the formula:

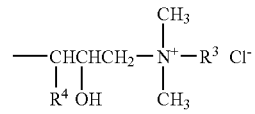

wherein R$^3$ is selected from $C_1$ to $C_{24}$ alkyl, benzyl and phenyl, and R$^4$ is chlorine or hydrogen.

6. A method as set forth in claim 1 wherein said personal care composition comprises an ingredient selected from an auxiliary hydrocolloid, a rheology modifier, an auxiliary fixative, a solvent, a propellant, and mixtures thereof.

7. A method as set forth in claim 6 wherein said personal care composition further comprises an ingredient selected from a pH adjusting agent, emulsifier(s), emollient(s), surfactant(s), conditioning agent(s), and mixtures thereof.

8. A method as set forth in claim 6 wherein said personal care composition further comprises an ingredient selected from therapeutic agent(s), hair colorant(s), hair bleaching agent(s), hair highlighting agent(s), botanical extract(s), oxidizing agent(s), reducing agent(s), preservative(s), fragrance(s), solubilizer(s), detangling agent(s), wet combing agent(s), and mixtures thereof.

9. A method as set forth in claim 6 wherein said hydrocolloid in said personal care composition is an non-derivatized polygalactomannan gum is selected from guar gum, *Cassia gum*, tara gum, locust bean gum, fenugreek gum, and mixtures thereof.

10. A method as set forth in claim 6 wherein said rheology modifier in said personal care composition is selected from crosslinked copolymers of (meth)acrylic acid, crosslinked copolymers of (meth)acrylic acid and $C_1$-$C_5$ alkyl (meth)acrylate(s), crosslinked copolymers of (meth)acrylic acid and $C_{10}$-$C_{30}$ alkyl (meth)acrylate(s), HASE polymers, and acid swellable associative polymer(s).

11. A method as set forth in claim 10 wherein said rheology modifier in said personal care composition is Polyacrylate-1 Crosspolymer.

12. A method as set forth in claim 6 wherein said personal care composition is in the form of a spray, gel, pomade, and foam.

13. A personal care hair fixative composition comprising:
    a) a polygalactomannan having repeating units containing a D-mannosyl to D-galactosyl residue ratio of at least 5 to 1, said D-mannosyl and D-galactosyl residues having pendant hydroxyl groups, and wherein a portion of the hydrogen groups on the pendant hydroxy substituents on the mannosyl and galactosyl residues are substituted with a group represented by the formula:

-AR$^1$ wherein A is a substituted or unsubstituted alkylene group containing 1 to 6 carbon atoms, and
    R$^1$ is a group independently —N(R$^3$)$_3$$^+$X$^-$, —S(R$^3$)$_2$$^+$X$^-$, and
    —P(R$^3$)$_3$$^+$X$^-$; wherein R$^3$ independently represents substituted and unsubstituted $C_1$ to $C_{24}$ alkyl, substituted and unsubstituted benzyl and substituted and unsubstituted phenyl; and X is any suitable anion that balances the charge on the onium cation;
    b) an adjuvant selected from an emulsifier, an emollient, a conditioning agent, and mixtures thereof; and optionally
    c) non-derivatized guar gum.

14. A hair fixative composition of claim 13 wherein the weight ratio of said polygalactomannan to said guar gum ranges from 1:5 to 5:1.

15. A hair fixative composition of claim 12 wherein said -AR$^1$ moiety is represented by the formula:

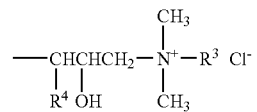

wherein R$^3$ is selected from $C_1$ to $C_{24}$ alkyl, benzyl and phenyl, and R$^4$ is chlorine or hydrogen.

16. A hair fixative composition of claim 15 wherein said -AR$^1$ moiety is 2-hydroxy-3-(trimethylammonium)propyl chloride.

* * * * *